_United States Patent_ [19]

Boltze et al.

[11] Patent Number: 4,647,560

[45] Date of Patent: Mar. 3, 1987

[54] NEW BENZODIAZEPINES AND THEIR USE

[75] Inventors: Karl-Heinz Boltze, Borod; Eugen Etschenberg, Cologne; Jörg Traber, Lohmar; Herbert Büsgen, Niederkassel, all of Fed. Rep. of Germany

[73] Assignee: Troponwerke GMBH & Co. KG, Cologne, Fed. Rep. of Germany

[21] Appl. No.: 763,746

[22] Filed: Aug. 8, 1985

[30] Foreign Application Priority Data

Aug. 24, 1984 [DE] Fed. Rep. of Germany ....... 3431195

[51] Int. Cl.$^4$ ..................... A61K 31/55; C07D 243/24
[52] U.S. Cl. .................................... 514/220; 540/495; 540/504; 514/221; 546/224; 546/212; 546/209; 546/214; 546/194
[58] Field of Search ................. 260/239.3 D, 239.3 T; 514/220, 221

[56] References Cited

U.S. PATENT DOCUMENTS 3,998,811 12/1976 Kajfez et al. ................ 260/239.3 D

FOREIGN PATENT DOCUMENTS 0045452 2/1982 European Pat. Off. ..... 260/239.3 D
2523250 12/1975 Fed. Rep. of Germany ... 260/239.3 D
3422411 1/1985 Fed. Rep. of Germany ........ 546/16

OTHER PUBLICATIONS

Bell et al., "J. Org. Chem.", vol. 27, (1962), pp. 562–566.

_Primary Examiner_—Robert T. Bond
_Attorney, Agent, or Firm_—Sprung Horn Kramer & Woods

[57] ABSTRACT

The present invention relates to novel benzodiazepines, acid addition salts thereof, processes for their preparation and their use in combating diseases, in particular for the treatment of cerebral disorders caused by old age and for the treatment of disorders in learning and memory and amnesia.

10 Claims, No Drawings

NEW BENZODIAZEPINES AND THEIR USE

The invention relates to new benzodiazepines and acid addition salts thereof, processes for their preparation and their use in combating diseases, in particular for the treatment of cerebral disorders caused by old age and for the treatment of disorders in learning and memory and amnesia.

The invention relates to benzodiazepines of the general formula I

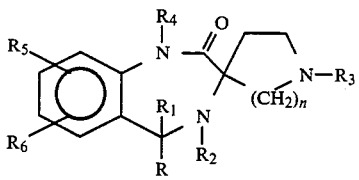

in which
R represents H, saturated or unsaturated, straight-chain, branched or cyclic alkyl, unsubstituted aralkyl or aralkyl which is optionally substituted in the aromatic part, unsubstituted for optionally substituted aryl or heteroaryl,
$R_1$ represents H,
$R_2$, $R_3$ and $R_4$ independently of one another represent H, alkyl or aralkyl which is unsubstituted or optionally substituted in the aromatic part, or, wherein $R_1$ and $R_2$ can also jointly form a bond,
$R_5$ and $R_6$ independently of one another represent H, halogen, nitro, cyano, trifluoromethyl, lower alkyl or lower alkoxy and
n represents an integer from 1 to 3.

Where the compounds can occur in the form of optical antipodes, the invention relates both to the racemate and to the individual enantiomers. The racemate can be split by the customary route by salt formation with an optically active acid and fractional crystallisation of the diastereomeric salts, or by chromatography on an optically active carrier material.

The benzodiazepines of the present invention clearly differ from the abundance of known benzodiazepines by their structure and their pharmacological action. The compounds according to the invention have no affinity for benzodiazepine receptors in the brain and, in animal experiments, show no anxiolytic action comparable to that of the benzodiazepines. In contrast to the known benzodiazepines, they have a potent psychotropic action in animal experiments. In the behavior test on healthy and brain-damaged rats, they lead to a clear improvement in learning ability and memory performance. The compounds according to the invention are therefore suitable for the treatment of disorders in cerebral function caused by old age, such as the various forms of presenile and senile dementia of the Alzheimer type.

Formula I provides a general definition of the benzodiazepines according to the invention.

Preferred compounds of the formula I are those in which
R represents H or straight-chain, branched or cyclic alkyl which has 1 to 8 carbon atoms and is saturated or contains a double bond, or represents an aralkyl radical with an alkyl or alkylene chain of 1 to 3 C atoms and a phenyl radical which is unsubstituted or optionally provided with one or two substituents from the series comprising Cl, Br, F, Cn, $CF_3$, $NO_2$, $CH_3$, $C_2H_5$ and $OCH_3$, or represents a phenyl radical which is optionally provided with one or two substituents from the series comprising Cl, F, Br, CN, $CF_3$, $NO_2$, $CH_3$, $C_2H_5$ and $OCH_3$, or represents a 5-membered or 6-membered aromatic radical with 1 or 2 heteroatoms from the series comprising O, N and S,
$R_1$ represents H,
$R_2$, $R_3$ and $R_4$ independently of one another represent H or an alkyl radical with 1 to 6 carbon atoms, or represent an aralkyl radical with an alkyl or alkylene chain of 1 to 3 C atoms and a phenyl radical which is unsubstituted or optionally provided with one or two substituents from the series comprising Cl, Br, F, CN, $CF_3$, $NO_2$, $CH_3$, $C_2H_5$ and $CH_3$, and wherein $R_1$ and $R_2$ can slso jointly form a bond, $R_5$ and $R_6$ independently of one another represent H, F, Cl, Br, CN, $CF_3$, $NO_2$, $CH_3$, $C_2H_5$ or $OCH_3$ and
n represents an integer from 1 to 3.

In the preferred benzodiazepines n particularly preferably denotes 2. Particularly preferred compounds of the formula I are those in which
R represents a phenyl radical which is unsubstituted or optionally provided with 1 or 2 substituents from the series comprising Cl, F, Br, CN, $CF_3$ and $NO_2$, or represents a 5-membered or 6-membered heteroaromatic radical with 1 or 2 heteroatoms from the series comprising O, N and S,
$R_1$ represents H,
$R_2$, $R_3$ and $R_4$ independently of one another represent H or an alkyl radical with 1 to 4 carbon atoms, and wherein $R_1$ and $R_2$ can also jointly form a bond, $R_5$ and $R_6$ independently of one another represent H, F, Cl, Br, CN, $CF_3$ or $NO_2$ and
n represents 2.

It has furthermore been found that the compounds of the formula I are obtained by a process in which compounds of the general formula II are cyclised with compounds of the general formula III to give compounds of the general formula IV

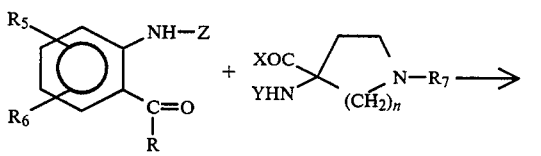

II          III

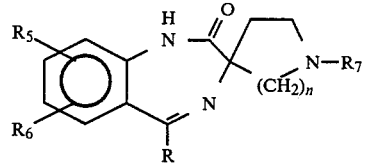

IV and, in the case where $R_7$ represents a protective group in the compounds of the formula IV thus obtained, this protective group is split off and optionally the radicals $R_2$ and $R_4$ are introduced by alkylation.

In the compounds of the formulae II and IV, the radicals $R_5$, $R_6$ and R have the abovementioned meaning and Z represents H or a protective group, such as, for example, trifluoroacetyl.

In the compounds of the formula III, COX represents a carboxyl function or an activated carboxyl func-tion, such as is used for the preparation of acid amide bonds, for example an ester function or a carboxylic acid chloride function.

Y represents H or a protective group customary in peptide chemistry, such as, for example, the carbobenzoxy group: (a) R. B. Merrifield, J. Biol. Chemie 232, 43 (1958); (b) J. P. Greenstein u. M. Wirnitz, Chemistry of the Amino Acids Vol. 2, p. 887 to 901; John Wiley & Sons, Inc., New York (1961.

$R_7$ in III and IV either has the abovementioned meaning of $R_3$ or represents a protective group, such as, for example, benzyl (T. W. Greene, Protective Groups in Organic Synthesis, p. 272; John Wiley & Sons, Inc., New York (1981).

Depending on the meaning of the radicals X, Y and Z, it is possible either to carry out the cyclisation reaction in one step or first to prepare the acid amine bond and then to link the C=N double bond, if appropriate after removal of the protective group Y, or first to produce the C=N double bond and, in the second step, to prepare the acid amide bond, if appropriate after removal of the protective group Z and activation of the carboxyl function. n generally denotes an integer from 1 to 3 and preferably denotes 2.

Compounds of the formula Ia can be obtained from compounds of the formula IV by removal of the protective group $R_7$.

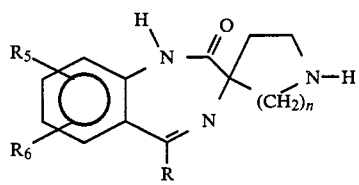
Ia

The alkylation reaction to introduce the radicals $R_2$ and/or $R_4$ can of course be carried out either before or after splitting off the protective group.

The compounds of the formula Ib ($R_3$=alkyl) are obtained from the compounds of the formula Ia by alkylation:

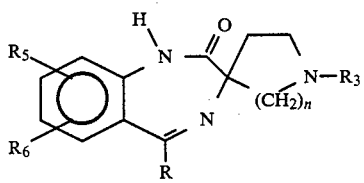
Ib and the compounds Ic ($R_3$ and $R_4$=alkyl) are obtained by a second alkylation reaction:

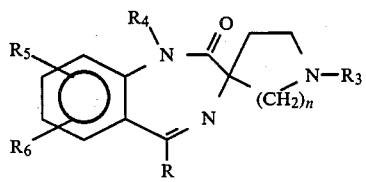
Ic

The compounds of the formula Id ($R_4$=alkyl)

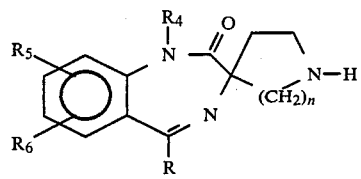
Id are obtained by alkylation of the compounds of the formula IV and subsequent removal of the protective group $R_7$.

Compounds of the formula Ie are obtained by hydrogenation.

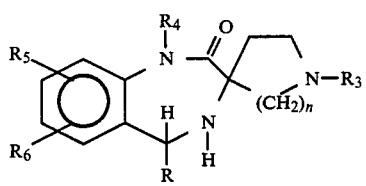
Ie of the double bond of unsaturated compounds of the formula I.

Alkylation of compounds of the formula Ie ($R_3$ and $R_4$=alkyl) gives compounds of the formula If ($R_2$, $R_3$ and $R_4$=alkyl):

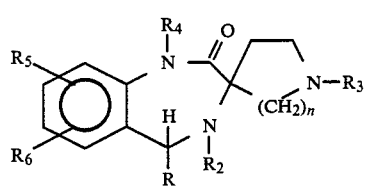
If

Compounds of the formula V can be obtained from compounds of the formula IV by saturation of the C=N double bond with $H_2$:

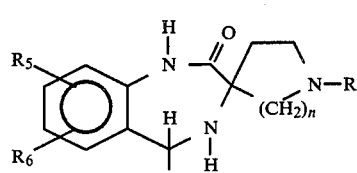
V

The compounds Ig ($R_2$=alkyl) and Ih ($R_2$ and $R_4$=alkyl) are obtained by mono- or di-alkylation of the compounds of the formula V and subsequent detachment of the protective group $R_7$:

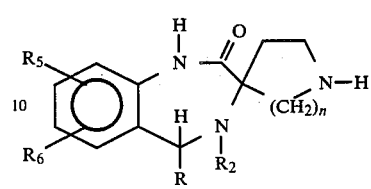
Ig

-continued

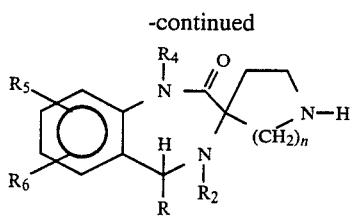
Ih

Finally, compounds of the formula Ii ($R_2$ and $R_3$=alkyl) are obtained from Ig ($R_2$=alkyl) by alkylation or from Ie ($R_3$ and $R_4$=H) by two reductive alkylations:

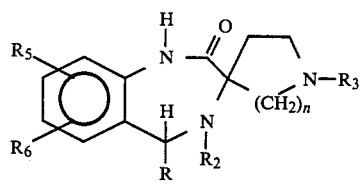
Ii

The preparation of the compounds of the formula 1 is illustrated by way of example by the following equation:

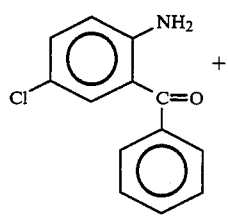

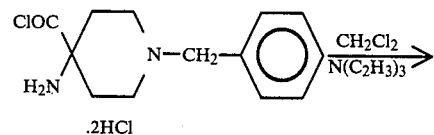

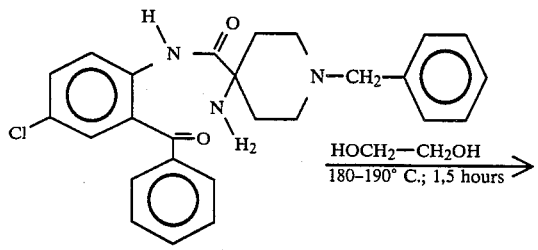

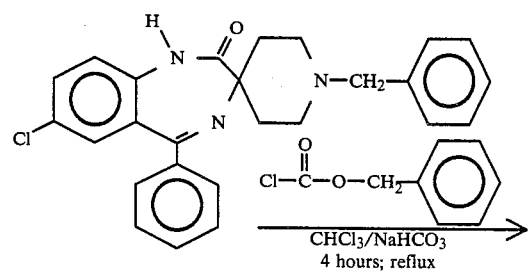

The following equations are intended to illustrate the preparation of other compounds of the formula I by way of example:

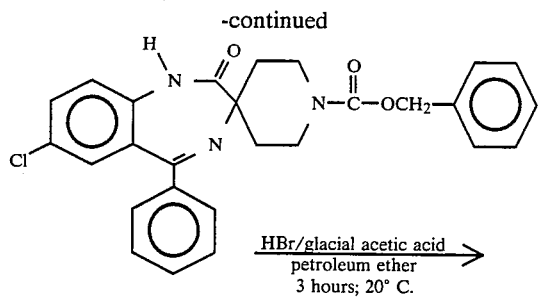

$$\xrightarrow[\text{3 hours; 20° C.}]{\text{HBr/glacial acetic acid} \atop \text{petroleum ether}}$$

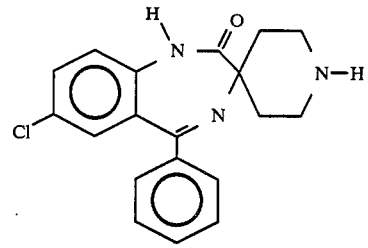

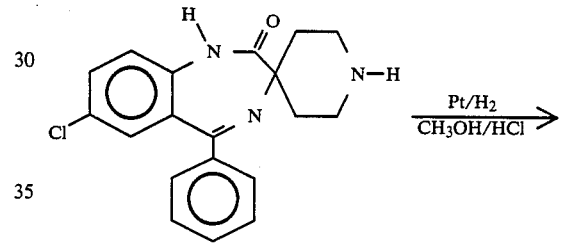

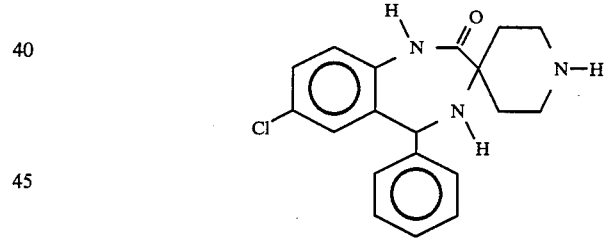

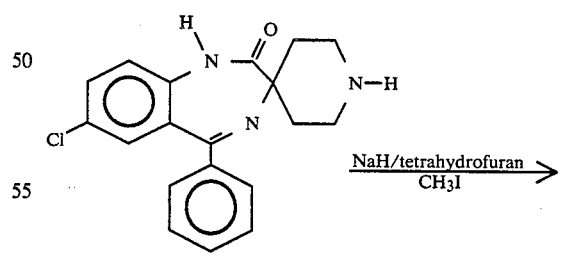

$$\xrightarrow[\text{CH}_3\text{I}]{\text{NaH/tetrahydrofuran}}$$

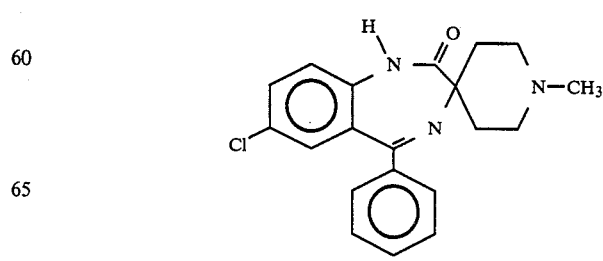

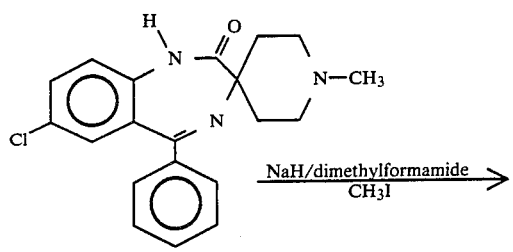

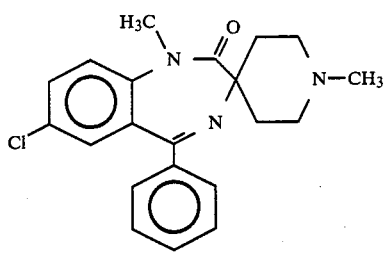

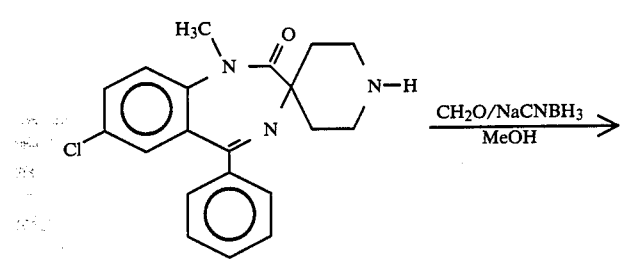

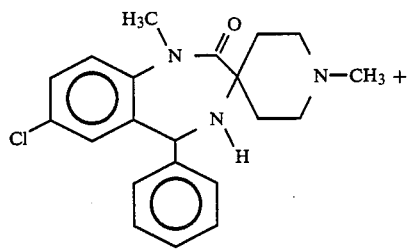

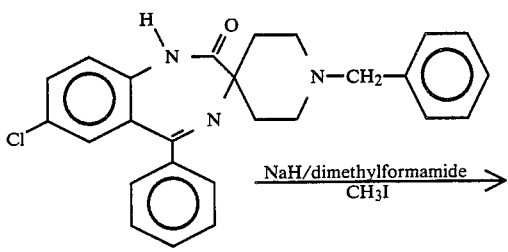

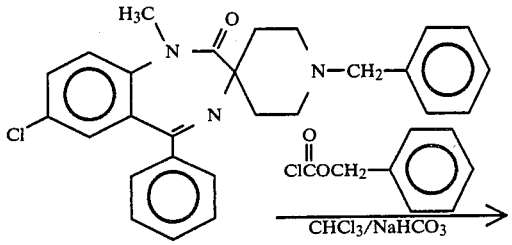

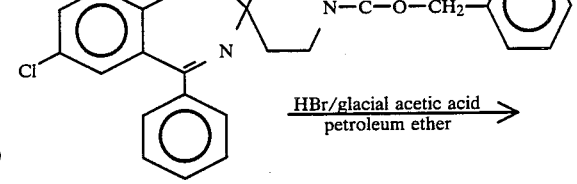

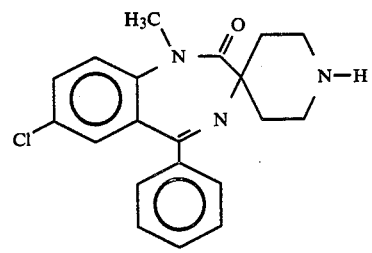

The reaction of the amino-ketones of the formula II (Z=H) with acid chlorides of the formula III (Y=H, X=Cl) is carried out in an inert solvent in the presence of a base to trap the hydrochloric acid. Preferred solvents are chlorinated hydrocarbons, such as methylene chloride or dichloroethane, ethers, such as tetrahydrofuran, dioxane or diethyl ether, or aromatic hydrocarbons, such as toluene. Possible auxiliary bases are tertiary amines, such as triethylamine, or inorganic bases, such as $NaHCO_3$ or potassium carbonate. The acid chlorides are employed in the reaction in the form of their bishydrochlorides. The reaction is carried out at temperatures between 0° C. and 50° C., preferably at room temperature.

The second reaction step for the preparation of compounds of the formula IV from compounds of the formulae II (Z=H) and III (Y=H, X=Cl), the cyclizing linking of the C=N double bond, is carried out by heating the open-chain intermediates in an inert, high-boiling solvent. Preferred solvents are dichlorobenzene or tetralin, and the use of ethylene glycol is particularly preferred. The reaction is carried out at temperatures between 130° C. and 230° C., preferably in a temperature range between 150° and 200° C. If appropriate, the water which forms can be removed azeotropically. The detachment of water can be catalyzed, if appropriate, by acids, such as p-toluenesulphonic acid.

The detachment of the protective group in the compounds of the formula IV is preferably carried out in two steps, the protective group radical first being replaced by a carbobenzoxy radical by reaction of the compounds IV with benzyl chlorocarbonate in an inert organic solvent in the presence of an inorganic auxiliary base. Solvents which are preferably used are chlorinated hydrocarbons, such as chloroform or dichloroethane, and preferred inorganic auxiliary bases are alkali metal carbonates or bicarbonates, such as K₂CO₃ or NaHCO₃. The reaction is carried out at temperatures between room temperature and the boiling point of the solvent, preferably at temperatures from 40° to 100° C. The carbobenzoxy protective group is then detached in the second step, preferably by a reaction with HBr/glacial acetic acid in the presence of an inert solvent.

The use of petroleum ether as the solvent is particularly preferred. The reaction is carried out at temperatures from 0° to 60° C., preferably at room temperature. It is preferable to use glacial acetic acid saturated with HBr to detach the carbobenzoxy protective group.

The double bond of the seven-membered ring of compounds of the formula I can be saturated with hydrogen by catalytic hydrogenation or by reaction with complex metal hydrides, such as NaBH₄. Catalytic hydrogenation with platinum as the catalyst at room temperature under normal pressure is preferred. Alcohols are preferably used as the solvents; alcohols, such as methanol, in the presence of hydrochloric acid are particularly preferred.

The alkylation of the three different NH functions in compounds of the formula I can be carried out by reaction with alkyl halides in the presence of an auxiliary base, such as K₂CO₃ or NaHCO₃, or after prior salt formation with NaH, or by reductive alkylation with aldehydes or ketones in the presence of NaCNBH₃. Solvents which are preferably used for alkylation with alkyl halides are aprotic solvents, such as tetrahydrofuran or dimethylformamide, and those which are preferably used for the reductive alkylation are alcohols, in particular methanol. The reaction is carried out at temperatures between 0° C. and the boiling point of the solvent; the reaction is preferably carried out at room temperature.

The amino-ketones of the formula II (Z=H) are known or, if they are new, can be prepared by methods analogous to those which are known per se, such as those described, for example, in Ehrhart and Ruschig, Arzneimittel (Drugs), 2nd edition, Volume 1, page 262, Verlag Chemie, Weinheim/Bergstrasse, 1972.

The aminoacid derivatives of the formula III are likewise known or can likewise be synthesised by processes analogous to those which are known per se (DOS (German Published Specification) No. 2,215,721).

New active benzodiazepines according to the invention which may be mentioned specifically are: 7-chloro-5-phenyl-spiro[1H-1,4-benzodiazepine-3,4'-piperidin]-2(3H)-one, 7-chloro-5-phenyl-1'-benzyl-spiro[1H-1,4-benzodiazepine-3,4'-piperidin]-2(3H)-one, 7-chloro-5-phenyl-1-methyl-spiro[1H-1,4-benzodiazepine-3,4'-piperidin]-2(3H)-one, 7-chloro-5-phenyl-1'-methyl-spiro[1H-1,4-benzodiazepine-3,4'-piperidin]-2(3H)-one, 7-chloro-5-phenyl-1'-benzyl-1-methyl-spiro[1H-1,4-benzodiazepine-3,4'-piperidin]-2(3H)-one, 7-chloro-5-phenyl-1,1'-dimethyl-spiro[1H-1,4-benzodiazepine-3,4'-piperidin]-2(3H)-one, 5-methyl-1'-benzyl-spiro[1H-1,4-benzodiazepine-3,4'-piperidin]-2(3H)-one, 7-chloro-4,5-dihydro-5-phenyl-spiro[1H-1,4-benzodiazepine-3,4'-piperidin]-2(3H)-one, 7-chloro-4,5-dihydro-5-phenyl-1-ethyl-spiro[1H-1,4-benzodiazepine-3,4'-piperidin]-2(3H)-one, 7-chloro-5-phenyl-1-ethyl-spiro[1H-1,4-benzodiazepine-3,4'-piperidin]-2(3H)-one, 7-chloro-4,5-dihydro-5-phenyl-1'-methyl-spiro[1H-1,4-benzodiazepine-3,4'-piperidin]-2(3H)-one, 7-chloro-4,5-dihydro-5-phenyl-1,1'-dimethyl-spiro[1H-1,4-benzodiazepine-3,4'-piperidin]-2(3H)-one, 7-chloro-4,5-dihydro-5-phenyl-1,1'-dimethyl-spiro[1H-1,4-benzodiazepine-1,4,1'-trimethyl-spiro[1H-1,4-benzodiazepine-3,4'-piperidin]-2(3H)-one, 7-chloro-4,5-dihydro-5-phenyl-4,1'-dimethyl-spiro[1H-1,4-benzodiazepine-3,4'-piperidin]-2(3H)-one, 7-chloro-4,5-dihydro-5-phenyl-1-methyl-spiro-[1H-1,4-benzodiazepine-3,4'-piperidin]-2(3H)-one, 7-chloro-5-(4-chlorophenyl)-1'-benzyl-spiro[1H-1,4-benzodiazepine-3,4'-piperidin]-2(3H)-one, 5-phenyl-1'-benzylspiro[1H-1,4-benzodiazepine-3,4'-piperidin]-2(3H)-one, 5-(2-(fluorophenyl)-1'-benzyl-spiro[1H-1,4-benzodiazepine-3,4'-piperidin]-2(3H)-one, 7-chloro-5-(2-chlorophenyl)-1'-benzyl-spiro[1H-1,4-benzodiazepine-3,4'-piperidin]-2(3H)-one, 7-chloro-5-(2-fluorophenyl)-1'-benzyl-spiro-[1H-1,4-benzodiazepine-3,4'-piperidin]-2(3H)-one, 8-methyl-5-phenyl-1'-benzyl-spiro[1H-1,4-benzodiazepine-3,4'-piperidin]-2(3H)-one, 7-chloro-5-(2-thienyl)-1'-benzyl-spiro[1H-1,4-benzodiazepine-3,4'-piperidin]-2(3H)-one, 7-chloro-5-(2-pyridyl)-1'-benzyl-spiro[1H-1,4-benzodiazepine-3,4'-piperidin]-2(3H)-one, 7-chloro-5-cyclohexyl-1'-benzyl-spiro[1H-1,4-benzodiazepine-3,4'-piperidin]-2(3H)-one, 7-chloro-5-isopropyl-1'-benzyl-spiro-[1H-1,4-benzodiazepine-3,4'-piperidin]-2(3H)-one, 7-chloro-5-butyl-1'-benzyl-spiro[1H-1,4-benzodiazepine-3,4'-piperidin]-2(3H)-one, 5-(4-methylphenyl)-1'-benzylspiro[1H-1,4-benzodiazepine-3,4'-piperidin]-2(3H)-one, 7-nitro-5-phenyl-1'-benzyl-spiro[1H-1,4-benzodiazepine-3,4'-piperidin]-2(3H)-one, 5-methyl-spiro[1H-1,4-benzodiazepine-3,4'-piperidin]-2(3H)-one, spiro[1H-1,4-benzodiazepine-3,4'-piperidin]-2(3H)-one, 7-chloro-5-(4-chlorophenyl)-spiro-[1H-1,4-benzodiazepine-3,4'-piperidin]-2(3H)-one, 5-phenyl-spiro-[1H-1,4-benzodiazepine-3,4'-piperidin]-2(3H)-one, 5-(2-fluorophenyl)-spiro-[1H-1,4-benzodiazepine-3,4'-piperidin]-2(3H)-one, 7-chloro-5-(2-fluorophenyl)-spiro-[1H-1,4-benzodiazepine-3,4'-piperidin]-2(3H)-one, 7-chloro-5-(2-chlorophenyl)-spiro-[1H-1,4-benzodiazepine-3,4'-piperidin]-2(3H)-one, 8-methyl-5-phenyl-spiro-[1H-1,4-benzodiazepine-3,4'-piperidin]-2(3H)-one, 7-chloro-5-(2-thienyl)-spiro-[1H-1,4-benzodiazepine-3,4'-piperidin]-2(3H)-one, 7-chloro-5-(2-pyridyl)-spiro-[1H-1,4-benzodiazepine-3,4'-piperidin]-2(3H)-one, 7-chloro-5-cyclohexyl-spiro-[1H-1,4-benzodiazepine-3,4'-piperidin]-2(3H)-one, 7-chloro-5-isopropyl-spiro-[1H-1,4-benzodiazepine-3,4'-piperidin]-2(3H)-one, 7-chloro-5-butyl-spiro-[1H-1,4-benzodiazepine-3,4'-piperidin]-2(3H)-one, 5-(4-methylphenyl)-spiro-[1H-1,4-benzodiazepine-3,4'-piperidin]-2(3H)-one, 7-nitro-5-phenyl-spiro-[1H-1,4-benzodiazepine-3,4'-piperidin]-2(3H)-one, 7-chloro-5-(3-furyl)-spiro-[1H-1,4-benzodiazepine-3,4'-piperidin]-2(3H)-one, 7-chloro-1-methyl-5-(3-furyl)-spiro-[1H-1,4-benzodiazepine-3,4'-piperidin]-2(3H)-one, 7-chloro-5-(2-thiazolyl)-spiro[1H-1,4-benzodiazepine-3,4'-piperidin]-2(3H)-one, 7-chloro-5-(1-methyl-2-pyrrolyl)-spiro-[1H-1,4-benzodiazepine-3,4'-piperidin]-2(3H)-one, 7-chloro-5-(2-furyl)-spiro-[1H-1,4-benzodiazepine-3,4'-piperidin]-2(3H)-one, 7-chloro-1-methyl-5-(2-furyl)-spiro-[1H-1,4-benzodiazepine-3,4'-piperidin]-2(3H)-one, 7-chloro-4,5-dihydro-5-(2-furyl)-spiro-[1H-1,4-benzo-diazepine-3,4'-piperidin]-2(3H)-one, 7-chloro-5-(3-thienyl)-spiro-[1H-1,4-benzodiazepine-3,4'-piperidin]-2(3H)-one, 7-chloro-5-(3,5-dimethyl-4-isoxazolyl)-spiro-[1H-1,4-benzodiazepine-3,4'-piperidin]-2(3H)-one, 7-chloro-1-methyl-5-(3,5-dimethyl-4-isoxazolyl)-spiro-[1H-1,4-benzodiazepine-3,4'-piperidin]-2(3H)-one, 7-chloro-5-(1-methyl-5-pyrazolyl)-spiro-[1H-1,4-benzodiazepine-3,4'-piperidin]-2(3H)-one, 7-chloro-1-methyl-5-(1-methyl-5-pyrazolyl)-spiro-[1H-1,4-benzodiazepine-3,4'- piperidin]-2(3H)-one, 7-cloro-5-(1-methyl-2-imidazolyl)-spiro-[1H-1,4-benzodiazepine-3,4′-piperidin]-2(3H)-one, 7-chloro-5-(3-pyridyl)-spiro-[1H-1,4-benzodiazepine-3,4′-piperidin]-2(3H)-one, 7-chloro-5-(4-pyridyl)-spiro-[1H-1,4-benzodiazepine-3,4′-piperidin]-2(3H)-one, 7-chloro-1-ethyl-5-(4-pyridyl)-spiro-[1H-1,4-benzodiazepine-3,4′-piperidin]-2(3H)-one, 7-chloro-5-(cyclohexen-1-yl)-spiro-[1H-1,4-benzodiazepine-3,4′-piperidin]-2(3H)-one, 7-chloro-spiro-[1H-1,4-benzodiazepine-3,4′-piperidin]-2(3H)-one, 7-chloro-1-methyl-spiro-[1H-1,4-benzodiazepine-3,4′-piperidin]-2(3H)-one, 7-chloro-1-methyl-4,5-dihydro-spiro-[1H-1,4-benzodiazepine-3,4′-piperidin]-2(3H)-one, 7-chloro-5-methyl-spiro-[1H-1,4-benzodiazepine-3,4′-piperidin]-2(3H)-one, 7-chloro-4,5-dihydro-5-methyl-spiro-[1H-1,4-benzodiazepine-3,4′-piperidin]-2(3)-one, 7-chloro-1,5-dimethyl-spiro-[1H-1,4-benzodiazepine-3,4′-piperidin]-2(3H)-one, 7-chloro-4,5-dihydro-1,5-dimethyl-spiro-[1H-1,4-benzodiazepine-3,4′-piperidin]-2(3H)-one, 7-chloro-5-ethyl-spiro-[1H-1,4-benzodiazepine-3,4′-piperidin]-2(3H)-one, 7-chloro-5-cyclopropyl-spiro-[1H-1,4-benzodiazepine-3,4′-piperidin]-2(3H)-one, 7-chloro-5-cyclopropylmethyl-spiro-[1H-1,4-benzodiazepine-3,4′-piperidin]-2(3H)-one, 7-chloro-5-benzyl-spiro-[1H-1,4-benzodiazepine-3,4′-piperidin]-2(3H)-one, 5-phenethyl-spiro-[1H-1,4-benzodiazepine-3,4′-piperidin]-2(3H)-one, 7-chloro-5-phenethyl-spiro-[1H-1,4-benzodiazepine-3,4′-piperidin]-2(3H)-one, 7-chloro-5-cinnamyl-spiro-[1H-1,4-benzodiazepine-3,4′-piperidin]-2(3H)-one, 7-chloro-5-allyl-spiro-[1H-1,4-benzodiazepine-3,4′-piperidin]-2(3H)-one, 7-chloro-5-(2-pyridylmethyl)-spiro-[1H-1,4-benzodiazepine-3,4′-piperidin]-2(3H)-one, 7-chloro-5-(4-pyridylmethyl)-spiro-[1H-1,4-benzodiazepine-3,4′-piperidin]-2(3H)-one, 7-chloro-5-(2-chloro-3-thienyl)-spiro-[1H-1,4-benzodiazepine-3,4′-piperidin]-2(3H)-one, 7-chloro-5-(5-isothiazolyl)-spiro-[1H-1,4-benzodiazepine-3,4′-piperidin]-2(3H)-one, 7-chloro-5-(4-cyanophenyl)-spiro-[1H-1,4-benzodiazepine-3,4′-piperidin]-2(3H)-one, 7-chloro-5-(2,4-dichlorophenyl)-spiro-[1H-1,4-benzodiazepine-3,4′-piperidin]-2(3H)-one, 5-(2,4-dichlorophenyl)-spiro-[1H-1,4-benzodiazepine-3,4′-piperidin]-2(3H)-one, 7-chloro-4,5-dihydro-5-(2,4-dichlorophenyl)-spiro-[1H-1,4-benzodiazepine-3,4′-piperidin]-2(3H)-one, 7-chloro-5-(2-iodophenyl)-spiro-[1H-1,4-benzodiazepine-3,4′-piperidin]-2(3H)-one, 7-chloro-5-(3-iodophenyl)-spiro-[1H-1,4-benzodiazepine-3,4′-piperidin]-2(3H)-one, 7-chloro-5-(4-iodophenyl)-spiro-[1H-1,4-benzodiazepine-3,4′-piperidin]-2(3H)-one, 7-chloro-5-(2-nitrophenyl)-spiro-[1H-1,4-benzodiazepine-3,4′-piperidin]-2(3H)-one, 7-chloro-5-(3-nitrophenyl)-spiro-[1H-1,4-benzodiazepine-3,4′-piperidin]-2(3H)-one, 7-chloro-5-(4-nitrophenyl)-spiro-[1H-1,4-benzodiazepine-3,4′-piperidin]-2(3H)-one, 7-chloro-5-(4-methylphenyl)-spiro-[1H-1,4-benzodiazepine-3,4′-piperidin]-2(3H)-one, 7-chloro-4,5-dihydro-5-(4-methylphenyl)-spiro-[1H-1,4-benzodiazepine-3,4′-piperidin]-2(3H)-one, 1-methyl-5-(4-methylphenyl)-spiro-[1H-1,4-benzodiazepine-3,4′-piperidin]-2(3H)-one, 7-nitro-1-methyl-5-phenyl-spiro-[1H-1,4-benzodiazepine-3,4′-piperidin]-2(3H)-one, 7-nitro-1-ethyl-5-phenyl-spiro-[1H-1,4-benzodiazepine-3,4′-piperidin]-2(3H)-one, 7-trifluoromethyl-5-phenyl-spiro-[1H-1,4-benzodiazepine-3,4′-piperidin]-2(3H)-one, 7-trifluoromethyl-4,5-dihydro-5-phenyl-spiro-[1H-1,4-benzodiazepine-3,4′-piperidin]-2(3H)-one, 7-methoxy-5-phenyl-spiro-[1H-1,4-benzodiazepine-3,4′-piperidin]-2(3H)-one, 7-methoxy-4,5-dihydro-5-phenyl-spiro-[1H-1,4-benzodiazepine-3,4′-piperidin]-2(3H)-one, 7,9-dichloro-5-phenyl-spiro-[1H-1,4-benzodiazepine-3,4′-piperidin]-2(3H)-one, 7,9-dichloro-1-methyl-5-phenyl-spiro-[1H-1,4-benzodiazepine-3,4′-piperidin]-2(3H)-one, 7-cyano-5-phenyl-spiro-[1H-1,4-benzodiazepine-3,4′-piperidin]-2(3H)-one, 7-cyano-1-methyl-5-phenyl-spiro-[1H-1,4-benzodiazepine-3,4′-piperidin]-2(3H)-one, 7-bromo-5-phenyl-spiro-[1H-1,4-benzodiazepine-3,4′-piperidin]-2(3H)-one, 8-nitro-5-phenyl-spiro-[1H-1,4-benzodiazepine-3,4′-piperidin]-2(3H)-one, 9-nitro-5-phenyl-spiro-[1H-1,4-benzodiazepine-3,4′-piperidin]-2(3H)-one, 6,9-dichloro-5-phenyl-spiro-[1H-1,4-benzodiazepine-3,4′-piperidin]-2(3H)-one, 8-cyano-5-phenyl-spiro-[1H-1,4-benzodiazepine-3,4′-piperidin]-2(3H)-one, 8-ethyl-5-phenyl-spiro-[1H-1,4-benzodiazepine-3,4′-piperidin]-2(3H)-one, 6,8-dimethyl-5-phenyl-spiro-[1H-1,4-benzodiazepine-3,4′-piperidin]-2(3H)-one, 7,8-dimethoxy-5-phenyl-spiro-[1H-1,4-benzodiazepine-3,4′-piperidin]-2(3H)-one, 8-trifluoromethyl-5-phenyl-spiro-[1H-1,4-benzodiazepine-3,4′-piperidin]-2(3H)-one, 7-chloro-5-(2-methoxyphenyl)-spiro-[1H-1,4-benzodiazepine-3,4′-piperidin]-2(3H)-one, 7-chloro-5-(3-methoxyphenyl)-spiro-[1H-1,4-benzodiazepine-3,4′-piperidin]-2(3H)-one, 7-chloro-5-(4-methoxyphenyl)-spiro-[1H-1,4-benzodiazepine-3,4′-piperidin]-2(3H)-one, 7-trifluorophenyl(-5-(2-methoxyphenyl)-spiro-[1H-1,4-benzodiazepine-3,4′-piperidin]-2(3H)-one, 8-cyano-5-(3-methoxyphenyl)-spiro-[1H-1,4-benzodiazepine-3,4′-piperidin]-2(3H)-one, 7-nitro-5-(4-methoxyphenyl)-spiro-[1H-1,4-benzodiazepine-3,4′-piperidin]-2(3H)-one, 7-chloro-5-(2-trifluoromethylphenyl)-spiro-[1H-1,4-benzodiazepine-3,4′-piperidin]-2(3H)-one, 7-chloro-5-(3-trifluoromethylphenyl)-spiro-[1H-1,4-benzodiazepine-3,4′-piperidin]-2(3H)-one, 7-chloro-5-(4-trifluoromethylphenyl)-spiro-[1H-1,4-benzodiazepine-3,4′-piperidin]-2(3H)-one, 7-trifluoromethyl-5-(2-trifluoromethylphenyl)-spiro-[1H-1,4-benzodiazepine-3,4′-piperidin]-2(3H)-one, 5-(2-methoxyphenyl)-spiro-[1H-1,4-benzodiazepine-3,4′-piperidin]-2(3H)-one, 9-cyano-7,8-dimethyl-5-phenyl-spiro-[1H-1,4-benzodiazepine-3,4′-piperidin]-2(3H)-one, 7-chloro-5-(4-ethylphenyl)-spiro-[1H-1,4-benzodiazepine-3,4′-piperidine]-2(3H)-one, 7-chloro-5-(2-furyl(-1′-benzyl-spiro[1H-1,4-benzodiazepine-3,4′-piperidine]-2(3H)-one, 7-chloro-5-(2-thiazolyl)-1′-benzyl-spiro[1H-1,4-benzodiazepine-3,4′-piperidine]-2-(3H)-one, 7-chloro-5-methyl-1′-benzyl-spiro[1H-1,4-benzodiazepine-3,4′-piperidine]-2-(3H)-one, 7-bromo-5-phenyl-1′-benzyl-spiro[1H-1,4-benzodiazepine-3,4′-piperidine]-2(3H)-one, 7-trifluoromethyl-5-phenyl-1′-benzyl-spiro[1H-1,4-benzodiazepine-3,4′-piperidine]-2(3H)-one, 7-chloro-5-(3-iodophenyl)-1′-benzyl-spiro[1H-1,4-benzodiazepine-3,4′-piperidine]-2(3H)-one, 7-chloro-5-phenyl-spiro[1H,4-benzodiazepine-3,3′-pyrrolidine]-2(3H)-one, 1′,2′,3′,5′,6′,7′-hexahydro-7-chloro-5-phenyl-spiro[1H-1,4-benzodiazepine-3,4′-azepine]-2-(3H)-one.

The improving action on learning and memory of active substances according to the invention has been investigated, for example, in the following tests:

1. Learning of an Active Avoidance Behaviour

Rats are trained in a "two-way avoidance box" ("shuttle box") to run, after presentation of a sound and a light signal (CS), to run to the other side of the test cage within 10 seconds (CR). A false reaction or the absence of any is punished by a foot shock (UCS; 0.5 mA, maximum of 10 seconds) (literature: Y. Tamaki and Y. Kameyama, Pharmac. Biochem. Behav. 16, 943–947, 1982). 20 trials take place on each day of the experiment. The period intervening between the trials is 20–60 seconds. Overall, training is carried out on 3 successive days. Test substances which, after daily administration 15 or 30 minutes before the start of the test, increase the number of avoidance reactions in the course of the experiment or shorten the avoidance latency periods (time between CS and CR) in comparison with controls are attributed a learning-improving action.

An example is shown in Table 1:

TABLE 1

| Day of experiment | Mean value of the avoidance latency periods in seconds (per 20 trials, n = 10) | |
|---|---|---|
| | Control | Example 8 (10 mg/kg/day, p.o.) |
| 1 | 8.2 | 7.1 |
| 2 | 8.0 | 5.4** |
| 3 | 6.8 | 4.8* |

**$p \leq 0.01$, t (28) = 2.82;
*$p \leq 0.05$, t (28) = 2.28

2. Water Labyrinth

Male rates are trained in a watertank (120×50 cm) to swim round a series of vertical barriers and to find the exit of the water labyrinth (literature: C. Giurgea and Mouravieff-Lesuisse, J. Pharmacol. Paris 3, 17–30, 1972). During the individual experimental trials, which are carried out at an interval of 1 to 3 days, the number of false swimming directions is measured. The reduction in the number of errors on successive trials are the parameter for the rate of learning of the experimental animals. If rats who have been treated daily with a test substance show a greater reduction in the number of errors during the course of the experiment than untreated control animals, the substance is attributed a learning-improving action. Such tests are carried out with intact rats of various ages and with rats in which a learning deficit has been experimentally induced (for example by electrical or chemical lesions in the brain).

An example is shown in Table 2.

TABLE 2

| Experimental trial | Number of administrations (in each case 5 mg/kg i.p.) | Type of experimental animals, age | Mean value of the number of errors (n = 10/group) | |
|---|---|---|---|---|
| | | | Control | Example 1 |
| 1 | 0 | intact, | 23 | 23 |
| 5 | 4 | 6 months | 7 | 3 |
| 1 | 0 | intact, | 15 | 15 |
| 4 | 5 | 20 months | 19 | 8** |
| 1 | 0 | Hippocampus lesions, | 20 | 21 |
| 5 | 4 | 6 months | 19 | 12* |
| 1 | 0 | Hippocampus lesions, | 29 | 29 |
| 7 | 10 | 6 months | 19 | 7** |

**p 0.05 Mann-Whitney U test (1)
*p 0.01 Mann-Whitney U test (1)
(1) S. Siegel, Nonparametric statistics for the behavioral sciences. McGraw-Hill, Kogakusha, Ltd.

The present invention includes pharmaceutical formulations which, in addition to non-toxic, inert, pharmaceutically suitable excipients, contain one or more of the compounds according to the invention or salts thereof, or consist of one or more of the compounds according to the invention or salts thereof, and to processes for the preparation of these formulations.

The present invention also include pharmaceutical formulations in dosage units. This means that the formulations are in the form of individual parts, for example tablets, dragees, capsules, pills, suppositories and ampules of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half, one-third or one-quarter of a daily dose.

By non-toxic, inert, pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminium metahydroxide, bentonite, agar-agar and tragacanth, or mixture of these substances.

The formulation forms mentioned can also contain colorants, preservatives and additives which improve the odor and flavor for example peppermint oil and eucalyptus oil, and sweeteners, for example saccharin.

The therapeutically active compounds should preferably be present in the abovementioned pharmaceutical formulations in a concentration of about 0.1 to 99.5% by weight, preferably about 0.5 to 95% by weight, of the total mixture.

The abovementioned pharmaceutical formulations can also contain other pharmaceutical active compounds, in addition to the compounds of the formula (I) and/or salts thereof.

The abovementioned pharmaceutical formulations are prepared in a customary manner by known methods, for example by mixing the active compound or compounds with the excipient or excipients.

The present invention also includes the use of the compounds of the formula (I) and/or salts thereof and of pharmaceutical formulations containing one or more compounds of the formula (I) and/or salts thereof, in human medicine for the prevention, alleviation and/or cure of the abovementioned diseases.

The active compounds or the pharmaceutical formulations can preferably be administered orally, parenterally and/or rectally, preferably orally and parenterally, especially orally and intravenously.

In general, it has proved advantageous to administer the active compound or compounds in amounts of about 0.01 to about 10, preferably 0.1 to 1 mg/kg of body weight every 24 hours in the case of parenteral (intravenous or intramuscular) administration and in amounts of about 0.05 to about 100, preferably 0.1 to 10 mg/kg of body weight every 24 hours in the case of oral administration, if appropriate in the form of several individual doses, in order to achieve the desired results. An individual dose preferably contains the active compound or compounds in amounts of about 0.01 to about 30, in particular 0.05 to 3 mg/kg of body weight.

However, it may be necessary to deviate from the dosages mentioned, and in particular to do so as a function of the species and body weight of the subject to be treated, the nature and severity of the disease, the nature of the formulation and of the administration of the medicament and the period or interval within which administration takes place. Thus is can in some cases suffice to manage with less than the abovementioned amount of active compound, while in other cases the abovementioned amount of active compound must be exceeded. The particular optimum dosage required and the type of administration of the active compounds can easily be determined by anyone skilled in the art on the basis of his expert knowledge.

EXAMPLE 1

7-Chloro-5-phenyl-spiro[1H-1,4-benzodiazepine-3,4'-piperidin]-2(3)-one

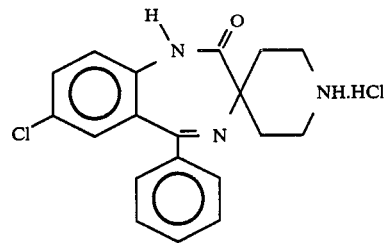

3.5 g (0.0073 mole) of 7-chloro-5-phenyl-N'-benzyloxycarbonyl-spiro[1H-1,4-benzodiazepine-3,4'-piperidin]-2(3H)-one are suspended in 50 ml of petroleum ether (40°–60° C.), and 6 ml of 38% strength HBr/glacial acetic acid solution are added at 0° C., with stirring. The reaction mixture is stirred at 20° C. for 3 hours and the hydrobromide formed is then filtered off with suction and washed 3 times with petroleum ether. The salt is dissolved in water and the aqueous solution is shaken with diethyl ether and rendered alkaline with 10% strength aqueous ammonia solution. The base liberated is taken up in methylene chloride and the organic phase is dried over $Na_2SO_4$ and filtered over active charcoal. The hydrochloride is precipitated from the methylene chloride solution by addition of a diethyl ether/HCl solution. The mixture is filtered and the salt is washed with diethyl ether and dried at 155° C. in vacuo over KOH. Sand-colored powder of melting point 225°–230° C.

Yield: 73% of theory.

Preparation of the starting compound:

7-Chloro-5-phenyl-1'-benzyloxycarbonyl-spiro[1H-1,4-benzodiazepine-3,4'-piperidin]-2(3H)-one

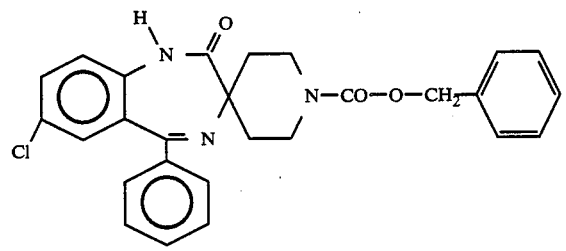

10 g (0.029 mole) of a 50% strength solution of benzyl chloroformate in toluene are added to a mixture of 4.0 g (0.0093 mole) of 7-chloro-5-phenyl-1'-benzyl-spiro[1H-1,4-benzodiazepine-3,4'-piperidin]-2-(3H)-one and 2.4 g (0.029 mole) of finely powdered $NaHCO_3$ in 80 ml of absolute chloroform. The reaction mixture is boiled for 3 hours, with reflux cooling. It is then poured onto ice and the organic phase is separated off and washed twice with 10% strength $NaHCO_3$ solution. After drying over $Na_2SO_4$, the mixture is filtered and the solvent is evaporated off. A pale brown-colored remains, and is crystallized with petroleum ether. The compound is filtered off with suction, washed with petroleum ether and dried at 60° C. in vacuo.

yeld: 4.0 g, corresponding to 90% of theory; melting point: 202°–204° C.

EXAMPLE 2

7-chloro-5-phenyl-1'-benzyl-spiro[1H-1,4-benzodiazepine-3,4'-piperidin]-2(3H)-one

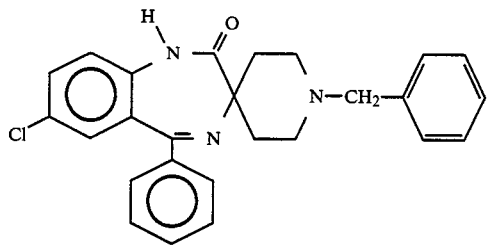

2.0 g (0.0044 mole) of N-(2-benzoyl-4-chlorophenyl)-4-amino-1-benzylpiperidinecarboxamide are heated at 180°–190° C. in 10 ml of ethylene glycol for 2 hours, with stirring. After the mixture has been cooled to room temperature, it is diluted with 30 ml of methylene chloride, and ice-water is added. The reaction product is extracted twice with methylene chloride and the combined organic phases are dried over $Na_2SO_4$, filtered and evaporated to dryness. The residue is purified by column chromatography on silica gel 60 (Merck). The column is eluted with a mixture of methylene chloride and methanol (9:1).

Yield: 1.5 g, corresponding to 79% of theory; melting point: 234° C.

Preparation of the starting compounds:

(a) 1-Benzyl-4-amino-4-piperidinocarboxylic acid 2'-benzoly-4'-chloroanilide

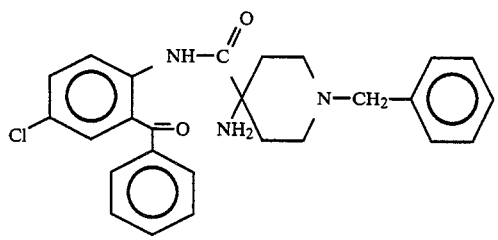

60 g (0.6 mole) of triethylamine are added dropwise to a mixture of 40 g (0.17 mole) of 2-amino-5-chloroacetophenone and 80 g (0.24 mole) of 1-benzyl-4-amino-4-piperidinecarboxylic acid chloride dihydrochloride in 900 ml of $CH_2Cl_2$ at 0° C. under $N_2$, with stirring. The mixture is stirred at 0° C. for one hour and at 20° C. for 2 hours. It is then poured onto ice, brought to pH 10 with NaOH and extracted with $CH_2Cl_2$. The dried $CH_2Cl_2$ extracts are concentrated to dryness. For purification, the residue is chromatographed on silica gel 60 (Merck). The column is eluted first with $CH_2Cl_2$/EE 3:2 and then with $CH_2Cl_2$/MeOH 9:1.

Yield: 46 g, corresponding to 51% of theory.

(b) 1-Benzyl-4-amino-4-piperidinecarboxylic acid chloride dihydrochloride

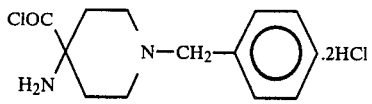

HCl is passed into a suspension of 10 g of finely powdered 1-benzyl-4-amino-4-piperidinecarboxylic acid in 111 ml of $CH_2Cl_2$ at 0° C. for 1 hour. 26 g of $PCl_5$ in 200 ml of $CH_2Cl_2$ are added in several portions to this mixture, with vigorous stirring and while passing in further HCl. After the mixture has been stirred at 0° C. for 4 hours, the reaction product is filtered off with suction over a glass frit, with exclusion of moisture, and washed thoroughly with petroleum ether (60°–80° C.) and $CH_2Cl_2$. The crude product thus obtained is used in the next reaction stage without further purification.

EXAMPLE 3

7-Chloro-5-phenyl-1-methyl-spiro[1H-1,4-benzodiazepine-3,4'-piperidin]-2(3H)-one

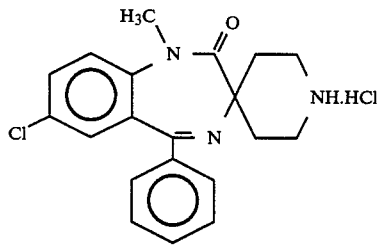

30 ml of an HBr/glacial acetic acid solution (about 38% strength) are added to 26 g (0.053 mole) of 7-chloro-1-methyl-5-phenyl-1'-benzyloxycarbonyl-spiro[1H-1,4-benzodiazepine-3,4'-piperidin]-2(3H)-one in 250 ml of petroleum ether (40°–60° C.) at 0° C., while stirring, and the mixture is left to react at room temperature for 8 hours. The supernatant petroleum ether is then decanted off, water is added to the viscous residue and the aqueous phase is brought to pH 10 with aqueous ammonia solution. The reaction product is extracted with methylene chloride and purified by preparative column chromatography on silica gel 60 (Merck); eluting agent; methanol/methylene chloride (1:9) with added ammonia (5% of a concentrated aqueous $NH_3$ solution).

Conversion into the crystalline hydrochloride is effected by taking up the oily base in methylene chloride and adding an HCl/diethyl ether solution.

Yield: 29% of theory; colorless crystals of melting point 200°–205° C.

Preparation of the starting compound:

The starting compound 7-chloro-1-methyl-5-phenyl-1'-benzyloxycarbonylspiro[1H-1,4-benzodiazepine-3,4'-piperidin]-2-(3H)-one is obtained analogously to Example 1 from 7-chloro-5-phenyl-1'-benzyl-1-methyl-spiro[1H-1,4-benzodiazepine-3,4'-piperidin]-2(3H)-one.

EXAMPLE 4

7-Chloro-5-phenyl-1'-methyl-spiro[1H-1,4-benzodiazepine-3,4'-piperidin]-2(3H)-one

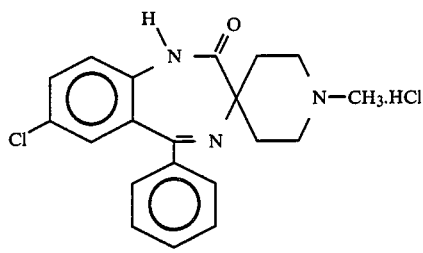

1 g (0.0029 mole) of 7-chloro-5-phenyl-spiro[1H-1,4-benzodiazepine-3,4'-piperidin]-2(3H)-one and 0.0029 mole of sodium hydride (55–60% strength dispersion) are stirred in 30 ml of absolute tetrahydrofuran at 25° C. for 30 minutes. After addition of 0.41 g (0.0029 mole) of methyl iodide at 0° C., the mixture is stirred at 0° C. for 1 hour and then at 25° C. for a further hour. The reaction mixture is then filtered, the solvent is evaporated off and 50 ml of water are added. After extraction with methylene chloride, the reaction product is purified by column chromatography on aluminum oxide 90, activity Level II-III (Merck); eluting agent: methylene chloride/cyclohexane/methanol (3:6:1).

After the solvent has been evaporated off, the oily base is obtained, and is taken up in diethyl ether and converted into the hydrochloride by addition of diethyl ether/HCL.

Yield: 56% of theory; colorless crystals of melting point 287° C.

Example 5

7-Chloro-5-phenyl-1'-benzyl-1-methyl-spiro[1H-1,4-benzodiazepine-3,4'-piperidin]-2(3H)-one

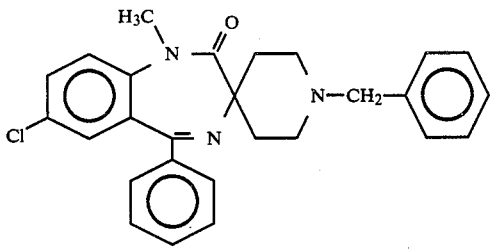

3.0 g (0.0069 mole) of 7-chloro-5-phenyl-1'-benzyl-spiro[1H-1,4-benzodiazepine-3,4'-piperidin]-2(3H)-one are dissolved in 25 ml of absolute dimethylformamide, and 0.3 g (0.007 mole) of sodium hydride (55–60% strength dispersion) is added at 20° C. After the mixture has been stirred for 20 minutes, it is cooled to 0° C., a solution of 1.0 g (0.0065 mole) of methyl iodide in 5 ml of absolute dimethylformamide is added dropwise and the mixture is stirred at 25° C. for 3 hours. The solvent is distilled off and the residue is purified by column chromatography over silica gel 60 (Merck). After the column has been eluted with methylene chloride/methanol (9:1), the oily base is obtained, which slowly crystallizes completely. Colorless crystals of melting point 169°–170° C.

Yield: 2.9 g, corresponding to 96% of theory.

EXAMPLE 6

7-Chloro-5-phenyl-1,1'-dimethyl-spiro[1H-1,4-benzodiazepine-3,4'-piperidin]-2(3H)-one

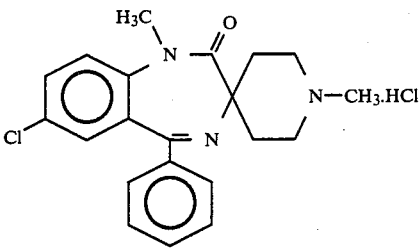

0.6 g (0.0016 mole) of 7-chloro-5-phenyl-1'-methyl-spiro[1H-1,4-benzodiazepine-3,4'-piperidin]-2(3H)-one are dissolved in 15 ml of absolute dimethylformamide and reacted with 0.1 g of sodium hydride (55–60% strength dispersion) at 70° C. After 30 minutes, the mixture is cooled to 25° C., 0.22 g (0.0016 mole) of methyl iodide in 10 ml of absolute dimethylformamide is added and the mixture is stirred for 2 hours. After the solvent has been distilled off, the residue is taken up in water and the mixture is extracted with methylene chloride. For purification, the product is chromatographed on aluminum oxide 90 (Merck), activity level II-III, with a cyclohexane/methylene chloride/methanol mixture (6:3:1), and the base thus obtained is converted into the hydrochloride by treatment with diethyl ether/HCl.

Yield: 0.4 g of hydrochloride; corresponding to 67% of theory; colorless crystals of melting point 214° C.

EXAMPLE 7

5-Methyl-1'-benzyl-spiro[1H-1,4-benzodiazepine-3,4'-piperidin]-2(3H)-one

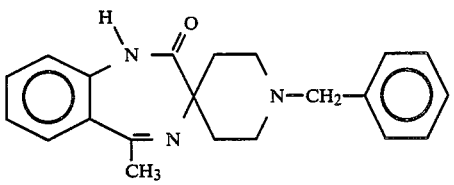

A solution of 12.2 g (0.12 mole) of triethylamine in 100 ml of methylene chloride is added dropwise to a mixture of 5.4 g (0.04 mole) of 2-aminocetophenone and 13.0 g (0.04 mole) of 1-benzyl-4-amino-4-piperidine-carboxylic acid chloride dihydrochloride (prepared from 9.4 g (0.04 mole) of 1-benzyl-4-amino-4-carboxypiperidine by reaction with excess phosphorus-V chloride in methylene chloride at 25° C.) in 400 ml of ethylene chloride at 0° C., while stirring and under an $N_2$ atmosphere, and the mixture is stirred at 0° C. for 1 hour and finally at 25° C. for 2 hours. It is then poured onto ice, the pH is brought to 10 with sodium hydroxide solution and the reaction product is extracted with methylene chloride. For purification, the product is chromatographed on silica gel 60 (Merck), a methylene chloride/methanol mixture (10:1) being used as the eluting agent.

The evaporated eluates give a colorless product which is recrystallized from methanol.

Yield: 5.0 g, corresponding to 37% of theory, melting point: 218°–219° C.

EXAMPLE 8

7-Chloro-4,5-dihydro-5-phenyl-spiro[1H-1,4-benzodiazepine-3,4'-piperidin]-2(3H)-one

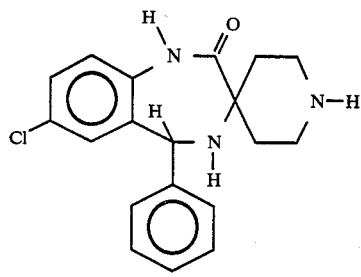

4.0 g (0.012 mole) of 7-chloro-5-phenyl-spiro[1H-1,4-benzodiazepine-3,4'-piperidin]-2(3H)-one are hydrogenated in 160 ml of methanol with the addition of 10 ml of a 30% strength isopropanol/HCl solution in the presence of platinum at 25° C. in the course of 3 hours, until the calculated amount of hydrogen has been taken up. After filtration, the solvent is distilled off, the residue is rendered alkaline with aqueous concentrated ammonia solution and the base is extracted by shaking with methylene chloride. The organic phase is washed with water, dried over $Na_2SO_4$ and concentrated and the residue is chromatographed on silica gel 60 (Merck); eluting agent: methylene chloride/methanol/25% strength aqueous ammonia solution (14:2.5:0.5).

Yield: 3.3 g, corresponding to 80% of theory; melting point: 135° C.; colorless crystals.

EXAMPLE 9

7-Chloro-4,5-dihydro-5-phenyl-1-ethyl-spiro[1H-1,4-benzodiazepine-3,4'-piperidin]-2(3H)-one

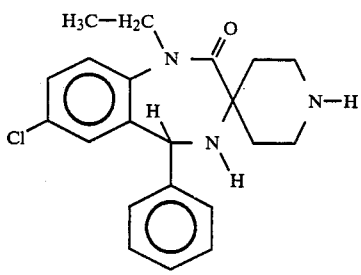

1.5 g (0.0041 mole) of 7-chloro-5-phenyl-1-ethyl-spiro[1H-1,4-benzodiazepine-3,4-piperidin]-2(3H)-one are hydrogenated in 35 ml of methanol with the addition of 4 ml of a 30% strength isopropanol/HCL solution in the presence of platinum at 25° C. in the course of 8 hours, until the calculated amount of hydrogen has been taken up.

The base obtained after working up is converted into the hydrochloride wih diethyl ether/HCl.

Yield: 1.0 g, corresponding to 73% of theory; melting point of the hydrochloride: 212° C.

Preparation of the starting compound:

The starting compound 7-chloro-5-phenyl-1-ethyl-spiro-[1H-1,4-benzodiazepine-3,4'-piperidin]-2(3H)-one is prepared analogously to Example 3.

EXAMPLE 10

7-Chloro-4,5-dihydro-5-phenyl-1'-methyl-spiro[1H-1,4-benzodiazepine-3,4'-piperidin]-2(3H)-one

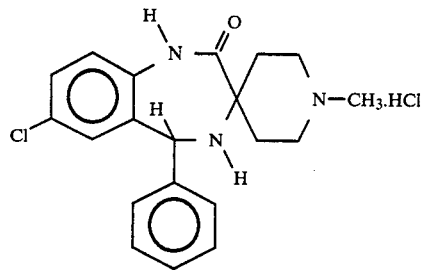

1.2 g (0.003 mole) of 7-chloro-5-phenyl-1'-methyl-spiro[1H-1,4-benzodiazepine-3,4'-piperidin]-2(3H)-one hydrochloride are hydrogenated in 40 ml of methanol with 4 ml of a 30% strength isopropanol/HCl solution in the presence of platinum at 25° C. in the course of 2 hours, until the calculated amount of hydrogen has been taken up.

The hydrogenation product obtained after working up is purified on silica gel 60 (Merck) by column chromatography. Eluting agent: methylene chloride methanol/25% strength aqueous $NH_3$ solution (9:1:0.2).

The base is converted into the hydrochloride with diethyl ether/HCl. Colorless crystals of melting point 260°–270° C.

Yield: 0.8 g of hydrochloride, corresponding to 68% of theory.

EXAMPLE 11

7-Chloro-4,5-dihydro-5-phenyl-1,1'-dimethyl-spiro[1H-1,4-benzodiazepine-3,4'-piperidin]-2(3H)-one and 7-Chloro-4,5-dihydro-5-phenyl-1,4,1'-trimethyl-spiro-[1H-1,4-benzodiazepine-3,4'-piperidin]-2(3H)-one

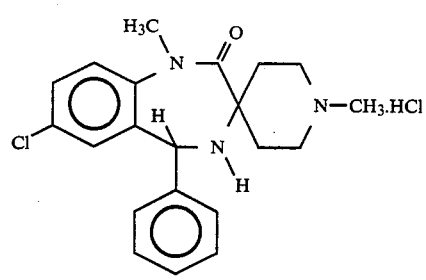

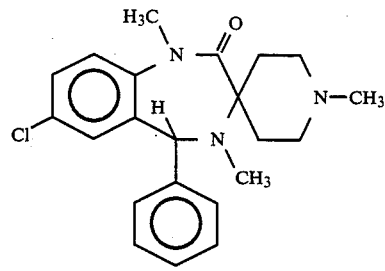

3.5 g (0.05 mole) of glacial acetic acid and 30 g of molecular sieve 3 Å (Merck) are added to a mixture of 10 g (0.028 mole) of 7-chloro-5-phenyl-1-methyl-spiro-[1H-1,4-benzodiazepine-3,4'-piperidin]-2(3H)-one, 10.8 g (0.12 mole) of formaldehyde (38% strength solution in water) and 3.46 g (0.055 mole) of NaBH₃(CN) in 300 ml of methanol at 0° C., with stirring.

The temperature is allowed to rise to 25° C. in the course of 2 hours, the solvent is evaporated off in vacuo, ice-water is added to the residue and the pH is brought to 1 by addition of hydrochloric acid. When the decomposition has ended, the mixture is rendered alkaline with sodium hydroxide solution and the reaction product is extracted by shaking with ethyl acetate. For purification, the product is chromatographed on aluminum oxide 90, activity level II-III (Merck), with a solvent mixture of cyclohexane, methylene chloride and methanol (6:3:1).

0.22 g of 7-chloro-4,5-dihydro-5-phenyl-1,4,1'-trimethyl-spiro-[1H-1,4-benzodiazepine-3,4'-piperidin]-2(3H)-one is obtained from the first fractions of the eluate in the form of colorless crystals of melting point 80°-85° C.

Yield: 2% of theory.

6.1 g of 7-chloro-4,5-dihydro-5-phenyl-1,1'-dimethyl-spiro-[1H-1,4-benzodiazepine-3,4'-piperidin]-2(3H)-one are obtained from the following fractions. After conversion into the hydrochloride, the substance has a melting point of 196° C.

Yield: 58% of theory (as the hydrochloride).

EXAMPLE 12

7-Chloro-4,5-dihydro-5-phenyl-4,1'-dimethyl-spiro-[1H-1,4-benzodiazepine-3,4'-piperidin]-2(3H)-one

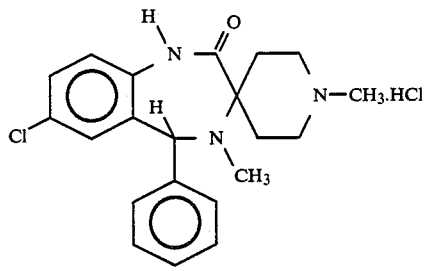

1.0 g (0.0029 mole) of 7-chloro-1b 5-phenyl-spiro-[1H-1,4-benzodiazepine-3,4'-piperidin]-2(3H)-one is dissolved in 30 ml of methanol, the solution is cooled to 0° C. and 4.2 g (0.053 mole) of formaldehyde (38% strength solution in water), 0.66 g (0.01 mole) of NaBH₃(CN), 1.0 g (0.016 mole) of glacial acetic acid and 3.0 g of molecular sieve 3 Å (Merck) are added in succession. The batch is then heated at 65° C. for 7 hours, the solvent is evaporated off in vacuo and the residue is acidified by addition of concentrated hydrochloric acid. When the decomposition has ended, the mixture is rendered alkaline with sodium hydroxide solution and the reaction product is extracted with ethyl acetate. For purification, the product is chromatographed on silica gel 60 (Merck) with a solvent mixture of methylene chloride, methanol and concentrated aqueous ammonia solution (9:1:0.2). The resulting oily base is converted into the hydrochloride with diethyl ether/HCl.

Colorless crystals, melting point: 198°-200° C.
Yield: 35% of theory.

EXAMPLE 13

7-Chloro-4,5-dihydro-5-phenyl-1-methyl-spiro-[1H-3,4-benzodiazepine-3,4'-piperidin]-2(3H)-one

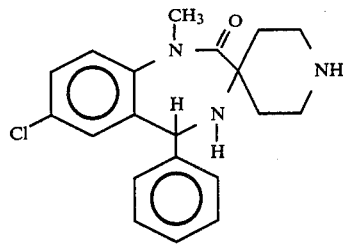

This compound was prepared analogously to Example 9 by hydrogenation of 7-chloro-5-phenyl-1-methyl-spiro-[1H-1,4-benzodiazepine-3,4'-piperidin]-2(3H)-one.

Melting point: 188°-190° C. (HCl salt).

EXAMPLE 14

7-Chloro-5-(4-chlorophenyl)-1'-benzyl-spiro-[1H-1,4-benzodiazepine-3,4'-piperidin]-2(3H)-one

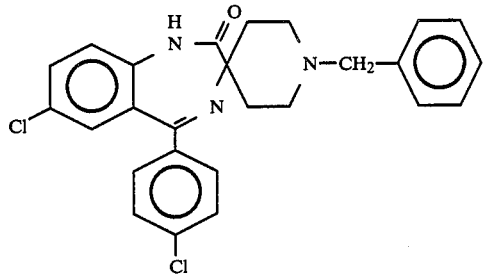

A solution of 11.4 g (0.043 mole) of 2-amino-4',5-dichlorobenzophenone in 150 ml of methylene chloride is added dropwise to a suspension of 1-benzyl-4-amino-4-piperidinecarboxylic acid chloride dihydrochloride (prepared from 10 g (0.043 mole) of 1-benzyl-4-amino-4-piperidinecarboxylic acid, as described above) in 120 ml of methylene chloride, while stirring and cooling with ice. 18 ml (0.13 mole) of triethylamine are then added dropwise and the mixture is stirred at room temperature for one hour and poured onto ice. After the mixture has been rendered alkaline with 2N sodium hydroxide solution, the organic phase is separated off, washed with water and dried over Na₂SO₄. The filtered solution is concentrated and the residue is purified by column chromatography on silica gel 60 (Merck); eluting agent: methylene chloride/methanol (100:3).

10.5 g of 1-benzyl-4-amino-4-piperidino-carboxylic acid 2'-(4-chlorobenzoyl)-4'-chloroanilide are obtained, and are subsequently cyclised by boiling in 200 ml of xylene in the presence of 0.5 g of p-toluene-sulphonic acid for 8 hours.

The residue obtained after distilling off the solvent is taken up in methylene chloride and the mixture is washed with sodium hydroxide solution and dried over Na₂SO₄. A pale yellow amorphous product, which crystallises from isopropanol, is obtained.

Yield: 9.5 g, corresponding to 48% of theory (based on the benzophenone derivative employed); melting point: 140° C.

The following xompounds were prepared analogously to Example 14:

| Example No. | Formula | Melting point (°C.) | Yield (% of theory) |
|---|---|---|---|
| 15 | 5-Phenyl-1'-benzyl-spiro[1H—1,4-benzodiazepine-3,4'-piperidin]-2(3H)—one | 209 | 64 |
| 16 | 5-(2-Fluorophenyl)-1'-benzyl-spiro[1H—1,4-benzodiazepine-3,4'-piperidin]-2(3H)—one | 215 | 38 |
| 17 | 7-Chloro-5-(2-chlorophenyl)-1'-benzyl-spiro[1H—1,4-benzodiazepine-3,4'-piperidin]-2(3H)—one | 246 | 18 |
| 18 | 7-Chloro-5-(2-fluorophenyl)-1'-benzyl-spiro[1H—1,4-benzodiazepine-3,4'-piperidin]-2(3H)—one | 206 | 13 |
| 19 | 8-Methyl-5-phenyl-1'-benzyl-spiro[1H—1,4-benzodiazepine-3,4'-piperidine]-2(3H)—one | 273 | 24 |
| 20 | 7-Chloro-5-(2-thienyl)-1'-benzyl-spiro[1H—1,4-benzodiazepine-3,4'-piperidin]-2(3H)—one | 235 | 81 |

-continued

| Example No. | Formula | Melting point (°C.) | Yield (% of theory) |
| --- | --- | --- | --- |
| | (structure with Cl, thiophene) | | |
| 21 | 7-Chloro-5-(2-pyridyl)-1'-benzyl-spiro[1H—1,4-benzodiazepine-3,4'-piperidin]-2(3H)—one | 226 | 73 |
| 22 | 7-Chloro-5-cyclohexyl-1'-benzyl-spiro[1H—1,4-benzodiazepine-3,4'-piperidin]-2(3H)—one | 199 | 23% |
| 23 | 7-Chloro-5-isopropyl-1'-benzyl-spiro[1H—1,4-benzodiazepine-3,4'-piperidin]-2(3H)—one | 182–183 | 56 |
| 24 | 7-Chloro-5-butyl-1'-benzyl-spiro[1H—1,4-benzodiazepine-3,4'-piperidin]-2(3H)—one | 105–106 | 48 |
| 25 | 5-(4-Methylphenyl)-1'-benzyl-spiro[1H—1,4-benzodiazepine-3,4'-piperidin]-2(3H)—one | 221 | 18 |

-continued

| Example No. | Formula | Melting point (°C.) | Yield (% of theory) |
|---|---|---|---|
| 26 | 7-Nitro-5-phenyl-1'-benzyl-spiro[1H—1,4-benzodiazepine-3,4'-piperidin]-2(3H)—one | 205 | 15 |
| 27 | 7-Chloro-5-(2-furyl)-1'-benzyl-spiro[1H—1,4-benzodiazepine-3,4'-piperidin]-2(3H)—one | 226–227 | 81 |
| 28 | 7-Chloro-5-(2-thiazolyl)-1'-benzyl-spiro[1H—1,4-benzodiazepine-3,4'-piperidin]-2(3H)—one | 214–215 | 82 |
| 29 | 7-Chloro-5-methyl-1'-benzyl-spiro[1H—1,4-benzodiazepine-3,4'-piperidin]-2(3H)—one | 221–222 | 48 |
| 30 | 7-Bromo-5-phenyl-spiro[1H—1,4-benzodiazepine-3,4'-piperidin]-2(3H)—one | 227–228 | 54 |
| 31 | 7-Trifluoromethyl-5-phenyl-1'-benzyl-spiro-[1H—1,4-benzodiazepine-3,4'-piperidin]-2(3H)—one | 173 | 60 |

-continued

| Example No. | Formula | Melting point (°C.) | Yield (% of theory) |
|---|---|---|---|
| 32 | 7-Chloro-5-(3-iodophenyl)-1'-benzyl-spiro[1H—1,4-benzodiazepine-3,4'-piperidin]-2(3H)—one 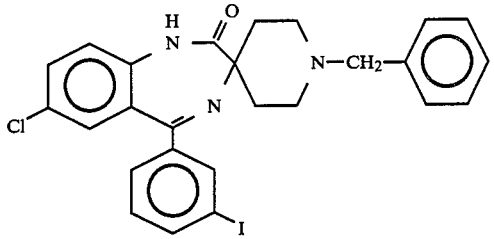 | 232 | 74 |

EXAMPLE 33

5-Methyl-spiro-[1H-1,4-benzodiazepine-3,4'-piperidin]-2(3H)-one

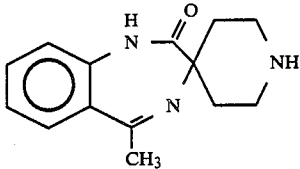

6.0 g (0.016 mole) of 5-methyl-1'-benzyloxycarbonyl-spiro-[1H-1,4-benzodiazepine-3,4'-piperidin]-2(3H)-one are hydrogenated in 250 ml of ethanol in the presence of 0.5 g of palladium-on-charcoal at 20° C. After the catalyst has been removed by filtration, the filtrate is concentrated and, after addition of diethyl ether, the residue crystallizes.

Yield: 3.5 g, corresponding to 90% of theory; melting point: 220°-222° C.

EXAMPLE 34

7-Chloro-5-(4-chlorophenyl)-spiro[1H-1,4-benzodiazepine-3,4'-piperidin]-2(3H)-one

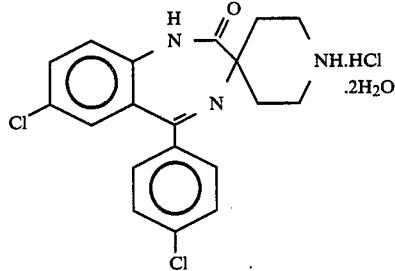

8.8 g (0.017 mole) of 5-(4-chlorophenyl)-7-chloro-1'-benzyloxycarbonyl-spiro[1H-1,4-benzodiazepine-3,4'-piperidin]-2(3H)-one are suspended in 150 ml of petroleum either (boiling range: 60°-80° C.), and 10 ml of 38 percent strength HBr/glacial acetic acid solution are added at 20° C., with stirring. The reaction mixture is stirred at room temperature for 6 hours and the crystalline product is filtered off with suction and rinsed with petroleum ether. The product is dissolved in water and the aqueous solution is shaken with diethyl ether and rendered alkaline with concentrated aqueous ammonia solution. The base which separates out is taken up in methylene chloride and the organic phase is dried over Na$_2$SO$_4$ and filtered. After evaporating off the solvent, the base is obtained in form of pale yellow crystals.

Yield: 5.2 g, corresponding to 80% of theory; melting point: 204°-206° C.

Hydrochloride:

14 ml of 1N hydrochloric acid are added to 5.2 g (0.014 mole) of the resulting base and the solution is evaporated in vacuo. 5-(4-Chlorophenyl)-7-chloro-spiro[1H-1,4-benzodiazepine,3,4'-piperidin]-2(3H)-one hydrochloride dihydrate is obtained.

Yield: 5.9 g, corresponding to 95% of theory; melting point >250° C. (decomposition).

The following compounds were prepared analogously to Example 34:

| Example No. | Formula | Melting point (°C.) | Yield (% of theory) |
|---|---|---|---|
| 35 | 5-Phenyl-spiro[1H—1,4-benzodiazepine-3,4'-piperidin]-2(3H)—one | 170 | 59 |

-continued

| Example No. | Formula | Melting point (°C.) | Yield (% of theory) |
|---|---|---|---|
| | [structure] | | |
| 36 | 5-(2-Fluorophenyl)-spiro[1H—1,4-benzodiazepine-3,4'-piperidin]-2(3H)—one [structure] | 206 | 73 |
| 37 | 7-Chloro-5-(2-fluorophenyl)-spiro[1H—1,4-benzodiazepine-3,4'-piperidin]-2(3H)—one [structure] | 170 | 68 |
| 38 | 7-Chloro-5-(2-chlorophenyl)-spiro[1H—1,4-benzodiazepine-3,4'-piperidin]-2(3H)—one [structure] | 182 | 85 |
| 39 | 8-Methyl-5-phenyl-spiro[1H—1,4-benzodiazepine-3,4'-piperidin]-2(3H)—one [structure, NH·HCl] | 260 | 97 |
| 40 | 7-Chloro-5-(2-thienyl)-spiro[1H—1,4-benzodiazepine-3,4'-piperidin]-2(3H)—one | 157–159 | 92 |

-continued

| Example No. | Formula | Melting point (°C.) | Yield (% of theory) |
|---|---|---|---|
| | (structure: 7-chloro benzodiazepinone spiro piperidine with 2-thienyl substituent) | | |
| 41 | 7-Chloro-5-(2-pyridyl)-spiro[1H—1,4-benzodiazepine-3,4'-piperidin]-2(3H)—one (structure shown with NH·2HCl) | >260 (decomposition) | 73 |
| 42 | 7-Chloro-5-cyclohexyl-spiro[1H—1,4-benzodiazepine-3,4'-piperidin]-2(3H)—one (structure shown) | 125 | 51 |
| 43 | 7-Chloro-5-isopropyl-spiro[1H—1,4-benzodiazepine-3,4'-piperidin]-2(3H)—one (structure shown with NH·HCl·H$_2$O) | decomposition from 150 | 96 |
| 44 | 7-Chloro-5-butyl-spiro[1H—1,4-benzodiazepine-3,4'-piperidin]-2(3H)—one (structure shown with CH$_2$CH$_2$CH$_2$CH$_3$) | 127–128 | 80 |
| 45 | 5-(4-Methylphenyl)-spiro[1H—1,4-benzodiazepine-3,4'-piperidin]-3(3H)—one (structure shown) | 214–216 | 93 |

-continued

| Example No. | Formula | Melting point (°C.) | Yield (% of theory) |
|---|---|---|---|
| 46 | 7-Nitro-5-phenyl-spiro[1H—1,4-benzodiazepine-3,4'-piperidin]-2(3H)—one | 260 | 97 |
| 47 | 7-Chloro-5-(2-furyl)-spiro[1H—1,4-benzodiazepine-3,4'-piperidin]-2(3H)—one | 159–160 (with decomposition) | 86 |
| 48 | 7-Chloro-5-(2-thiazolyl)-spiro[1H—1,4-benzodiazepine-3,4'-piperidin]-2(3H)—one | 140 | 85 |
| 49 | 7-Chloro-5-methyl-spiro[1H—1,4-benzodiazepine-3,4'-piperidin]-2(3H)—one | 240 (with decomposition) | 75 |
| 50 | 7-Bromo-5-phenyl-spiro[1H—1,4-benzodiazepine-3,4'-piperidin]-2(3H)—one | 156 | 92 |
| 51 | 7-Trifluoromethyl-5-phenyl-spiro[1H—1,4-benzodiazepin-3,4'-piperidin]-2(3H)—one | 227 | 95 |

-continued

| Example No. | Formula | Melting point (°C.) | Yield (% of theory) |
|---|---|---|---|
| 52 | 7-Chloro-5-(3-iodophenyl)-spiro[1H—1,4-benzodiazepine,3,4'-piperidin]-2(3H)—one | 218 | 96 |

EXAMPLE 53

7-Chloro-5-(4-chlorophenyl)-1'-benzyloxycarbonyl-spiro-[1H-1,4-benzodiazepine-3,4'-piperidin]-2(3H)-one

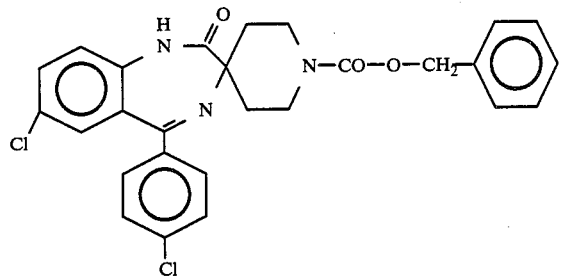

20 ml (0.06 mole) of a 50 percent strength solution of benzyl chloroformate in toluene are added to a mixture of 9.5 g (0.02 nole) of 7-chloro-5-(4-chlorophenyl)-1'-benzyl-spiro[1H-1,4-benzodiazepine-3,4'-piperidin]-2(3H)-one and 5 g (0.06 mole) of NaHCO₃ in 150 ml of methylene chloride. The reaction mixture is boiled for 3 hours, with reflux cooling. It is then poured onto ice and the organic phase is separated off and washed twice with 10 percent strength NaHCO₃ solution. After drying over Na₂SO₄, the organic phase is filtered and the solvent is evaporated off. The oily residue is made to crystallise with petroleum ether. The compound is filtered off with suction, boiled up with n-hexane and dried at 60° C. in vacuo.

Yield: 8.8 g, corresponding to 83% of theory; melting point: 130° C.

The following compounds werde prepared analogously to Example 53:

| Example No. | Formula | Melting point (°C.) | Yield (% of theory) |
|---|---|---|---|
| 54 | 5-Phenyl-1'benzyloxycarbonyl-spiro[1H—1,4-benzodiazepine-3,4'-piperidin]-2(3H)-one | 196 | 90 |
| 55 | 5-(2-Fluorophenyl)-1'-benzyloxycarbonyl-spiro[1H—1,4-benzodiazepine-3,4'-piperidin]-2-(3H)-one | 178 | 87 |

-continued

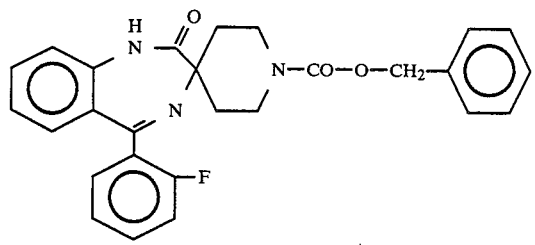

| 56 | 5-(2-Fluorophenyl)-7-chloro-1'-benzyloxycarbonyl-spiro[1H—1,4-benzodiazepine-3,4'-piperidin]-2(3H)one | 173 | 68 |

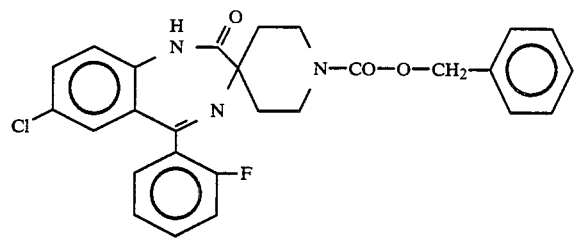

| 57 | 5-(2-Chlorophenyl)-7-chloro-1'-benzyloxycarbonyl-spiro[1H—1,4-benzodiazepine-3,4'-piperidin]-2(3H)-one | 166 | 93 |

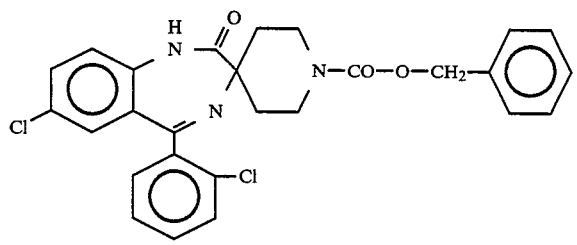

| 58 | 8-Methyl-1'-benzyloxycarbonyl-spiro[1H—1,4-benzodiazepine-3,4'-piperidin]-2(3H)one | 187 | 73 |

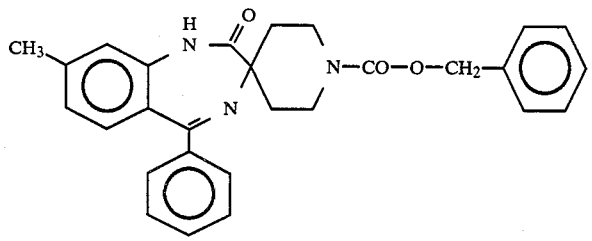

| 59 | 7-Chloro-5-(2-thienyl)-1'-benzyloxycarbonyl-spiro[1H—1,4-benzodiazepine-3,4'-piperidin]-2(3H)-one | 180–181 | 57 |

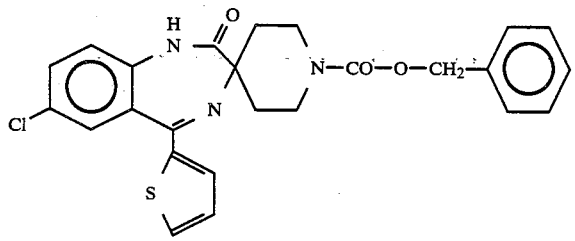

| 60 | 7-Chloro-5-(2-pyridyl)-1'-benzyloxycarbonyl-spiro[1H—1,4-benzodiazepine-3,4'-piperidin]-2(3H)-one | 213–214 | 91 |

-continued

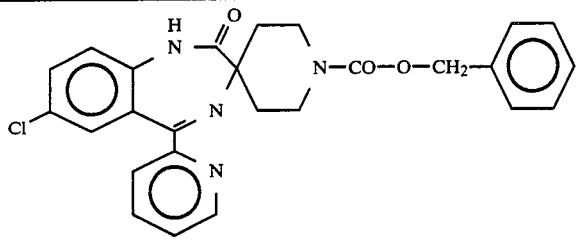

| 61 | 7-Chloro-5-cyclohexyl-1'-benzyloxycarbonyl-spiro[1H—1,4-benzodiazepine-3,4'-piperidin]-2(3H)-one | 239–240 | 91 |

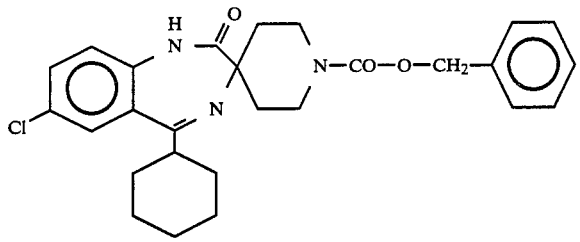

| 62 | 5-Methyl-1'-benzyloxycarbonyl-spiro[1H—1,4-benzodiazepine-3,4'-piperidin]-2(3H)one | 159–160 | 95 |

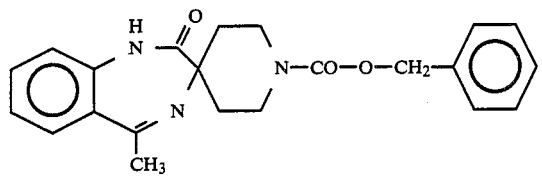

| 63 | 7-Chloro-5-isopropyl-1'-benzyloxycarbonyl-spiro[1H—1,4-benzodiazepine-3,4'-piperidin]-2(3H)-one | 215–218 | 72 |

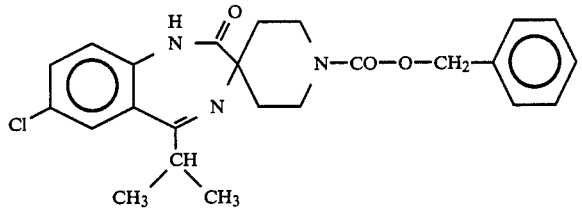

| 64 | 7-Chloro-5-butyl-1'-benzyloxycarbonyl-spiro[1H—1,4-benzodiazepine-3,4'-piperidin]-2(3H)-one | 176–177 | 85 |

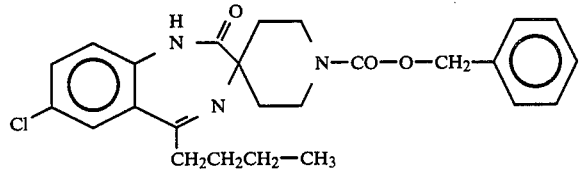

| 65 | 5-(4-Methylphenyl)-1'-benzyloxycarbonyl-spiro[1H—1,4-benzodiazepine-3,4'-piperidin]-2(3H)-one | 149 | 62 |

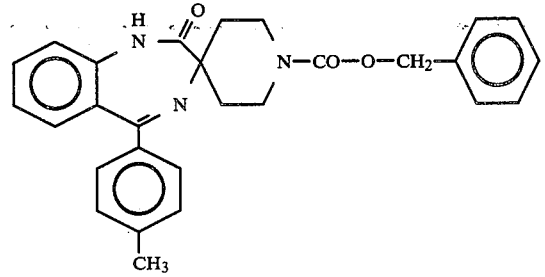

| 66 | 7-Nitro-5-phenyl-1'-benzyloxycarbonyl-spiro[1H—1,4-benzodiazepine-3,4'-piperidin]- | | |

| | | | |
|---|---|---|---|
| | 2(3H)-one | 135° | 94 |

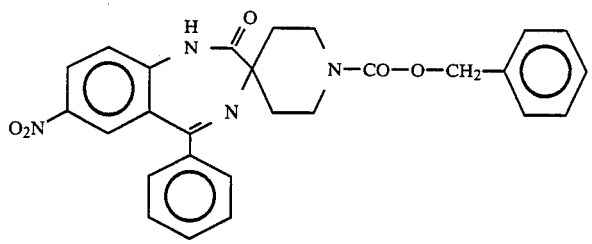

Preparation of anilides as intermediates:
The anilides are prepared analogously to Example 2 and 14.
The anilides are further used directly as crude products, without additional purification.
In the following examples some of the anilides are described:

| | | | |
|---|---|---|---|
| 67 | 7-Chloro-5-(2-furyl)-1'-benzyloxycarbonyl-spiro[1H—1,4-benzodiazepine-3,4'-piperidin]-2(3H)-one | 176–177 | 85 |

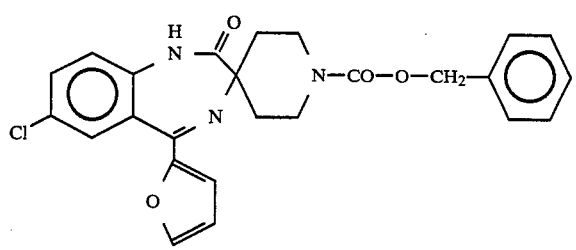

| | | | |
|---|---|---|---|
| 68 | 7-Chloro-5-(2-thiazolyl)-1'-benzyloxycarbonyl-spiro[1H—1,4-benzodiazepine-3,4'-piperidin]-2(3H)-one | 215–216 | 87 |

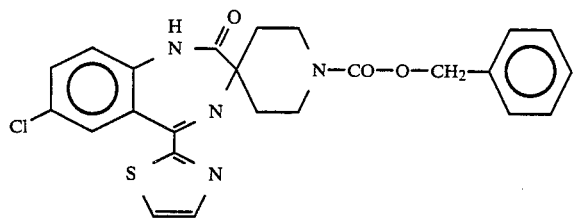

| | | | |
|---|---|---|---|
| 69 | 7-Chloro-5-methyl-1'-benzyloxycarbonyl-spiro[1H—1,4-benzodiazepine-3,4'-piperidin]-2(3H)-one | 147–148 | 98 |

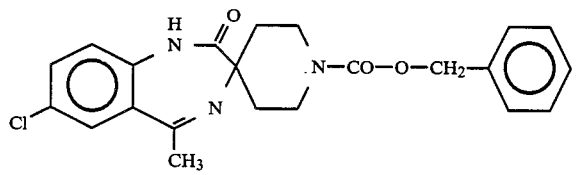

| | | | |
|---|---|---|---|
| 70 | 7-Bromo-5-phenyl-1'-benzyloxycarbonyl-spiro[1H—1,4-benzodiazepine-3,4'-piperidin]-2(3H)-one | 203–204 | 88 |

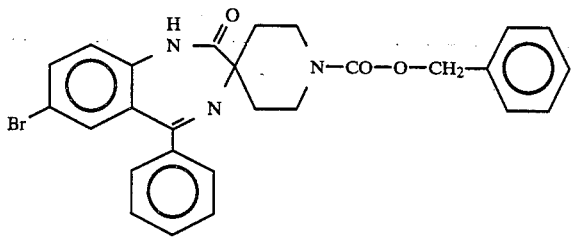

| | | | |
|---|---|---|---|
| 71 | 7-Trifluoromethyl-5-phenyl-1'-benzyloxycarbonyl-spiro[1H—1,4-benzodiazepine-3,4'-piperidin]-2(3H)-one | 100 | 42 |

-continued

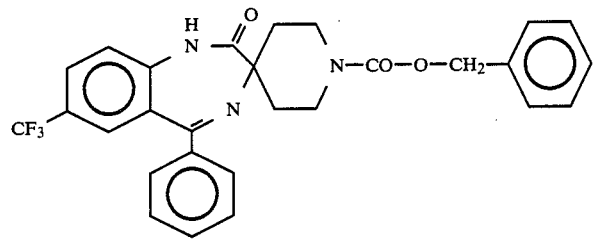

| | | | |
|---|---|---|---|
| 72 | 7-Chloro-5-(3-iodophenyl)-1'-benzyloxycarbonyl-spiro[1H—1,4-benzodiazepine-3,4'-piperidin]-2(3H)-one | 179 | 74 |

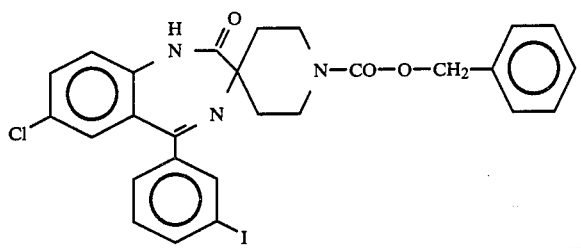

| Example No. | Amino-ketone | Anilide | Melting point (°C.) | Yield (% of theory) |
|---|---|---|---|---|
| 73 | | 1-Benzyl-4-amino-4-piperidino carboxylic acid 2'-benzoylanilide | oil | ~80 |

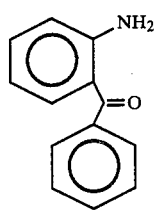 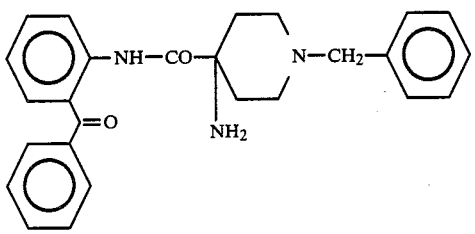

| | | | | |
|---|---|---|---|---|
| 74 | | 1-Benzyl-4-amino-4-piperidino carboxylic acid 2'-(2-fluorobenzoyl)-aniline | oil | ~53 |

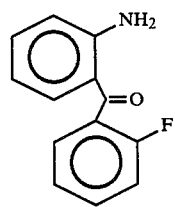 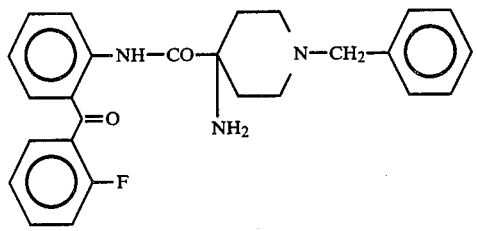

| | | | | |
|---|---|---|---|---|
| 75 | | 1-Benzyl-4-amino-4-piperidino carboxylic acid 2'-(2-fluorobenzoyl)-4'-chloroanilide | 135–8 | ~45 |

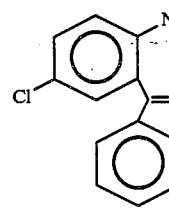 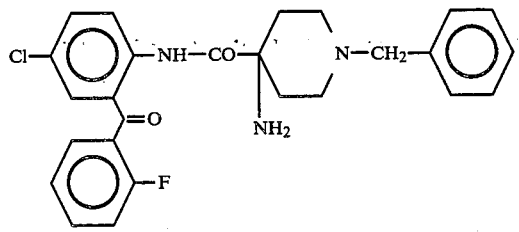

| | | | | |
|---|---|---|---|---|
| 76 | | 1-Benzyl-4-amino-4-piperidino carboxylic acid 2'-(2-chlorobenzoyl)-4'-chloroanilide | oil | ~38 |

| | | | |
|---|---|---|---|
| 77 | 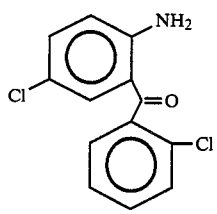 | 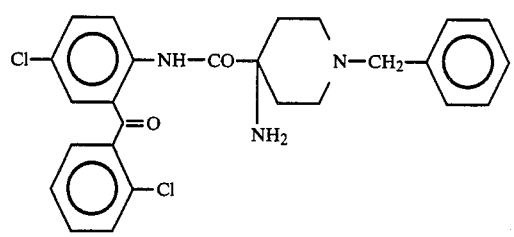  1-Benzyl-4-amino-4-piperidino carboxylic acid 2'-(4-chlorobenzoyl)-4'-chloroanilide | oil 51 |
| | L. H. Sternbach et al. J. Org. Chem. 26, 4488 (1962) 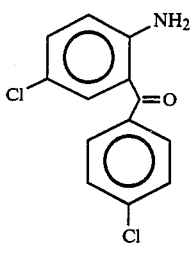 | 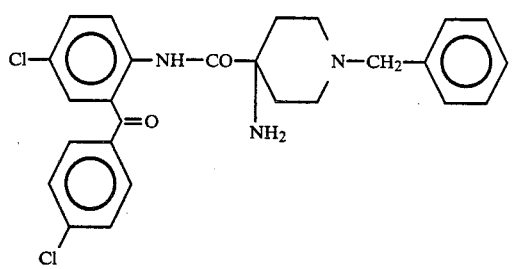 | |
| 78 | 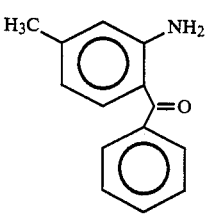 | 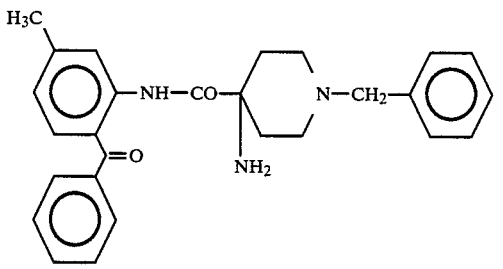  1-Benzyl-4-amino-4-piperidino carboxylic acid 2'-benzoyl-5'methylanilide | oil 40 |
| 79 | 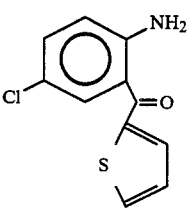  F. Hunziker et al. Eur. J. Chem. 16, 391 (1981) | 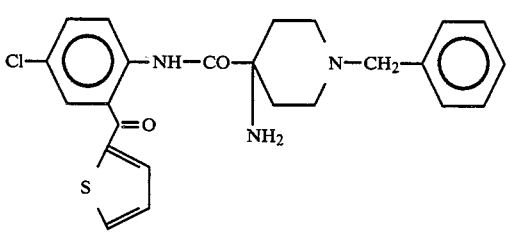  1-Benzyl-4-amino-4-piperidino carboxylic acid 2'-(2-thienoyl)-4'-chloroanilide | oil 42 |
| 80 | 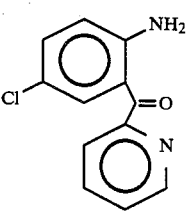 | 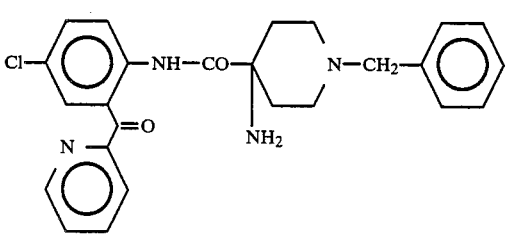  1-Benzyl-4-amino-4-piperidino carboxylic acid 2'-(2-pyridocarbonyl)-4'-chloroanilide | oil 41 |

R. I. Fryer et al.
J. Pharm. Sci. 53,
264 (1964)

| | | | | |
|---|---|---|---|---|
| 81 | 1-Benzyl-4-amino-4-piperidino carboxylic acid 2'-acetylanilide | | oil | 38 |

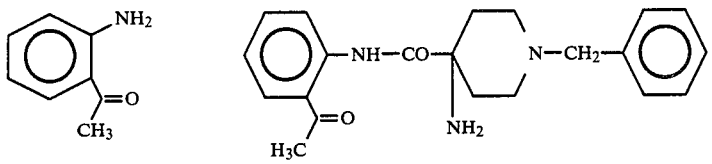

| | | | | |
|---|---|---|---|---|
| 82 | 1-Benzyl-4-amino-4-piperidino carboxylic acid 2'-(2-methylbutyryl)-4'-chloroanilide | | oil | 56 |

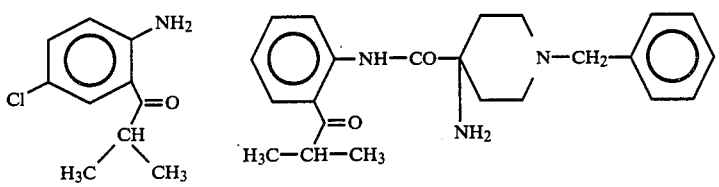

French Patent 1,391,752
(CA 63, 4361 (1965))

| | | | | |
|---|---|---|---|---|
| 83 | 1-Benzyl-4-amino-4-piperidino carboxylic acid 2'-valeroyl-4'-chloroanilide | | 100–103 | 61 |

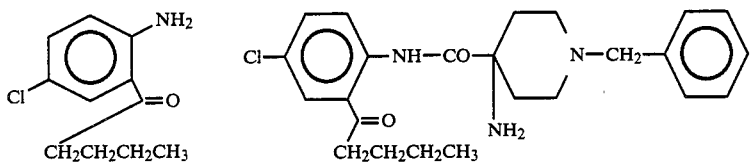

French Patent 1,391,752
(CA 63, 4361 (1965))

| | | | | |
|---|---|---|---|---|
| 84 | 1-Benzyl-4-amino-4-piperidino carboxylic acid 2'-cyclohexanoyl)-4'-chloroanilide | | 164 | 40 |

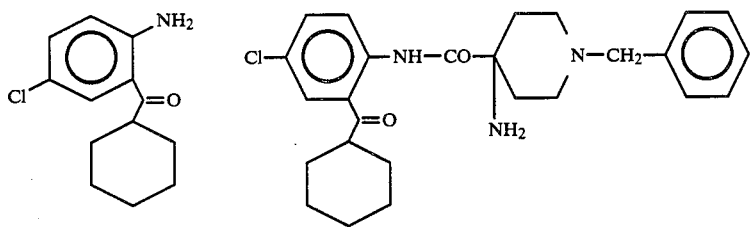

S. C. Bell et al.
J. Med. Pharm. Chem. 5,
63 (1962)

| | | | | |
|---|---|---|---|---|
| 85 | 1-Benzyl-4-amino-4-piperidino carboxylic acid 2'-benzoyl-4'-nitroanilide | | oil | 34 |

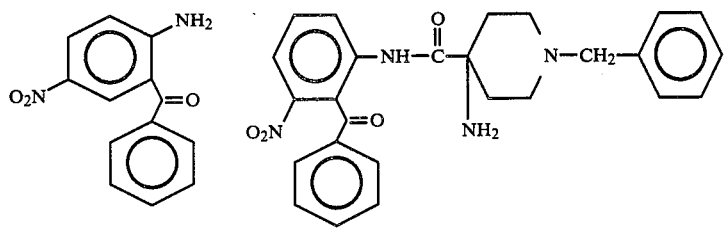

| | | | | |
|---|---|---|---|---|
| 86 | 1-Benzyl-4-amino-4-piperidino carboxylic acid | | oil | 38 |

-continued

| | | | |
|---|---|---|---|
| | 2'-(4-methylbenzoyl)-anilide | | |
| 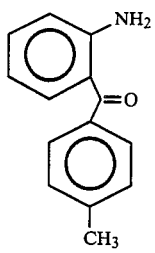 | 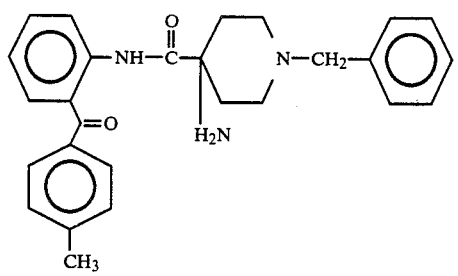 | | |
| 87 | 1-Benzyl-4-amino-4-piperidino carboxylic acid-2'-(2-furanoyl)-4'-chloroanilide | 132–133 | 59 |
| 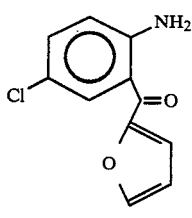 | 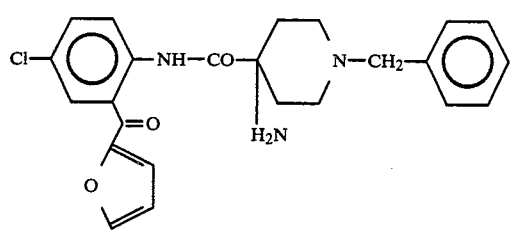 | | |
| 88 | 1-Benzyl-4-amino-4-piperidino carboxylic acid-2'-(2-thiazoyl)-4'-chloroanilide | 220–221 | 50 |
| 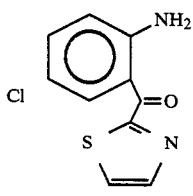 | 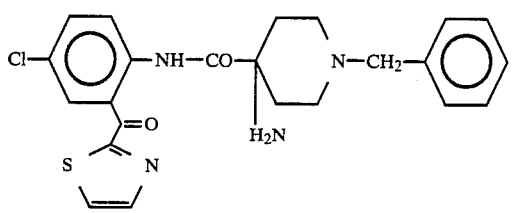 | | |
| 89 | 1-Benzyl-4-amino-4-piperidino carboxylic acid-2'-acetyl-4'-chloroanilide | 251–252 | 50 |
| 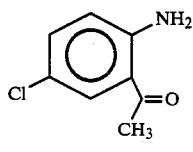 | 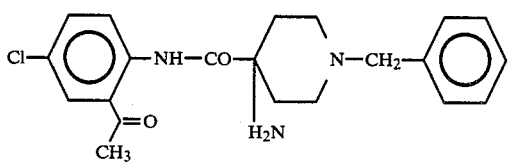 | | |
| 90 | 1-Benzyl-4-amino-4-piperidino carboxylic acid-2'-phenyl-4'-bromoanilide | oil | 50 |
| 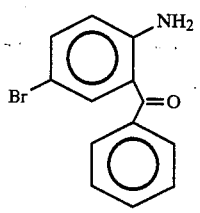 | 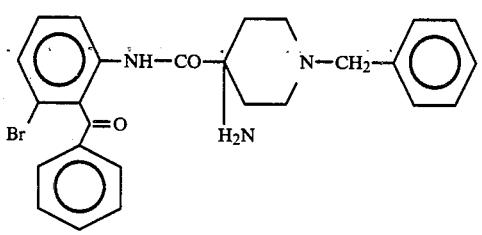 | | |
| 91 | 1-Benzyl-4-amino-4-piperidino carboxylic acid-2'-phenyl-4'-trifluoromethylanilide | oil | 51 |

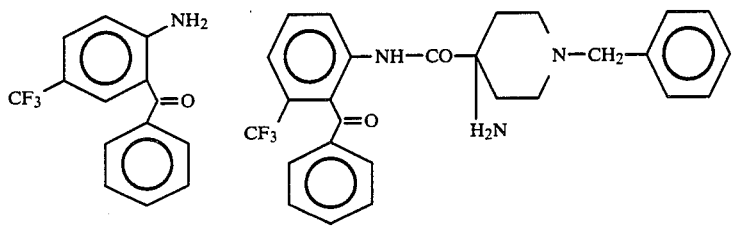
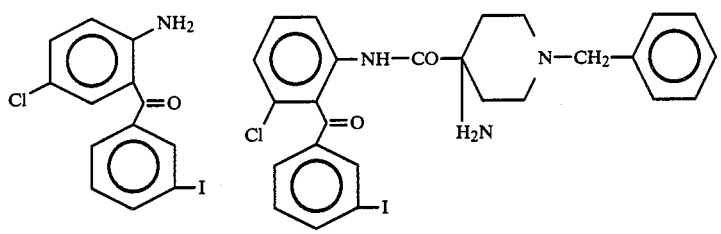

| 92 | 1-Benzyl-4-amino-4-piperidino carboxylic acid-2'-(3-iodophenyl)-4'-chloroanilide | 75-80 | 56 |

It is understood that the specification and examples are illustrative but not limitative of the present invention and that other embodiments within the spirit and scope of the invention will suggest themselves to those skilled in the are.

We claim:

1. A benzodiazepine of the formula

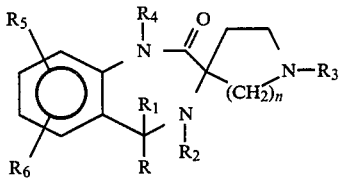

in which

R represents H alkyl, alkenyl, cycloalkyl or cycloalkenyl each with up to 8 carbon atoms; phenylalkyl with an alkylene chain of 1 to 3 C atoms and optionally substituted on the phenyl radical with one or two substituents selected from the group consisting of Cl, Br, F, CN, $CF_3$, $NO_2$, $CH_3$, $C_2H_5$ and $OCH_3$; or represents a phenyl radical which is optionally substituted with one or two substituents selected from the group consisting of Cl, F, Br, CN, I, $CF_3$, $NO_2$, $CH_3$, $C_2H_5$ and $OCH_3$; or represents a 5-membered or 6-membered heterocyclic radical with 1 or 2 heteroatoms from the group consisting of O, N and S, $R_1$ represents H or, together with $R_2$, forms a bond, and $R_2$, $R_3$ and $R_4$ independently of one another represent H or an alkyl radical with 1 to 6 carbon atoms, or represent a phenylalkyl radical with an alkyl chain of 1 to 3 C atoms and optionally substituted on the phenyl radical with one or two substituents selected from the group consisting of Cl, Br, F, CN, $CF_3$, $NO_2$, $CH_3$, $C_2H_5$ and $OCH_3$, or $R_2$ together with $R_1$, forms a bond, $R_5$ and $R_6$ independently of one another represent H, halogen, nitro, cyano, trifluoromethyl, lower alkyl or methoxy, and n represents an integer from 1 to 3.

2. A benzodiazepine according to claim 1, in which

R represents H, alkyl, alkenyl, or cycloalkyl or cycloalkenyl each with up to 8 carbon atoms; phenylalkyl with an alkylene chain of 1 to 3 C atoms and optionally substituted on the phenyl radical with one or two substituents selected from the group consisting of Cl, Br, F, CN, $CF_3$, $NO_2$, $CH_3$, $C_2H_5$ and $OCH_3$; or represents a phenyl radical which is optionally substituted with one or two substituents selected from the group consisting of Cl, F, Br, I, CN, $CF_3$, $NO_2$, $CH_3$, $C_2H_5$ and $OCH_3$; or represents thienyl, pyridyl, furyl or thiazolyl, $R_1$ represents H or, together with $R_2$, forms a bond, and $R_2$, $R_3$ and $R_4$ independently of one another represent H or an alkyl radical with 1 to 6 carbon atoms, or represent a phenylalkyl radical with an alkylene chain of 1 to 3 C atoms and optionally substituted on the phenyl radical with one or two substituents selected from the group consisting of Cl, Br, F, CN, $CF_3$, $NO_2$, $CH_3$, $C_2H_5$ and $OCH_3$, or $R_2$ together with $R_1$, forms a bond, $R_5$ and $R_6$ independently of one another represent H, halogen, nitro, cyano, trifluoromethyl, lower alkyl or methoxy, and n represents an integer from 1 to 3.

3. A benzodiazepine according to claim 1, in which

R represents H, alkyl, alkenyl, cycloalkyl or cycloalkenyl each with up to 8 carbon atoms; phenylalkyl with an alkylene chain of 1 to 3 atoms and optionally substituted on the phenyl radical with one or two substituents selected from the group consisting of Cl, Br, F, CN, $CF_3$, $NO_2$, $CH_3$, $C_2H_5$ and $OCH_3$; or represents a phenyl radical which is optionally substituted with one or two substituents selected from the group consisting of Cl, F, Br, CN, I, $CF_3$, $NO_2$, $CH_3$, $C_2H_5$ and $OCH_3$; or represents a thienyl, pyridyl, thiazolyl or furyl radical.

4. A benzodiazepine according to claim 1, in which

R represents a phenyl radical which is unsubstituted or optionally provided with 1 or 2 substituents from the group consisting of Cl, F, Br, CN, $CF_3$ and $NO_2$, or represents a 5-membered or 6-membered heteroaromatic radical with 1 or 2 heteroatoms from the group consisting of O, N and S, $R_1$ represents H or, together with $R_2$, forms a bond, $R_2$, $R_3$ and $R_4$ independently of one another represent H or an alkyl radical with 1 to 4 carbon atoms, or $R_2$, together with $R_1$, forms a bond, $R_5$ and $R_6$ independently of one another represent H, F, Cl, Br, CN, $CF_3$ or $NO_2$, and n represents 2.

5. A benzodiazepine from the group consisting of 7-chloro-5-phenyl-spiro[1H-1,4-benzodiazepine-3,4'-piperidin]-2(3H)-one, 7-chloro-5-phenyl-1'-benzyl-spiro[1H-1,4-benzodiazepine-3,4'-piperidin]-2(3H)-one, 7-chloro-5-phenyl-1-methyl-spiro[1H-1,4-benzodiazepin-3,4'-piperidin]-2(3H)-one, 7-chloro-5-phenyl-1'-methyl-spiro[1H-1,4-benzodiazepin-3,4'-piperidin]-2(3H)-one, 7-chloro-5-phenyl-1'-benzyl-1-methyl-spiro[1H-1,4-benzodiazepin-3,4'-piperidin]-2(3H)-one, 7-chloro-5-phenyl-1,1'-dimethylspiro[1H-1,4-benzodiazepin-3,4'-piperidin]-2(3H)-one, 5-methyl-1'-benzyl-spiro[1H-1,4-benzodiazepin-3,4'-piperidin]-2(3H)-one, 7-chloro-4,5-dihydro-5-phenyl-spiro]1H-1,4-benzodiazepine-3,4'-piperidin]-2(3H)-one, 7-chloro-4,5-dihydro-5-phenyl-1-ethyl-spiro]1H-1,4-benzodiazepin-3,4'-piperidin]-2(3H)-one, 7-chloro-4,5-dihydro-5-phenyl-1'-methyl-spiro[1H-1,4-benzodiazepin-3,4'-piperidin]-2(3H)-one, 7-chloro-4,5-dihydro-5-phenyl-1,1'-dimethylspiro]1H-1,4-benzodiazepin-3,4'-piperidin]-2(3H)-one, 7-chloro-4,5-dihydro-5-phenyl-1,4,1'-trimethyl-spiro[1H-1,4-benzodiazepin-3,4'-piperidin]-2(3H)-one and 7-chloro-4,5-dihydro-5-phenyl-4,1'-dimethyl-spiro-[1H-1,4-benzodiazepin-3,4'-piperidin]-2(3H)-one.

6. A benzodiazepine according to claim 1 which is 7-chloro-5-phenyl-spiro[1H-1,4-benzodiazepine-3,4'-piperidine]2(3H)-one of the formula

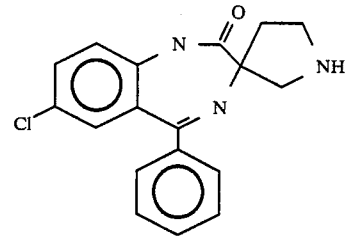

7. A composition for treating cerebral disorders comprising an amount effective therefor of a compound according to claim 1 in admixture with a diluent.

8. A unit dose of a composition according to claim 7 in the form of a tablet, capsule or ampule.

9. A method of treating a cerebral disorder which comprises administering to a patient in need thereof an amount effective therefor of a compound according to claim 1.

10. A method of treating a cerebral disorder which comprises administering to a patient in need thereof an amount effective therefor of a compound according to claim 5.

* * * * *

UNITED STATES PATENT AND TRADEMARK OFFICE
CERTIFICATE OF CORRECTION

PATENT NO. : 4,647,560

DATED : March 3, 1987

INVENTOR(S) : Karl-Heinz Boltze, et al.

It is certified that error appears in the above-identified patent and that said Letters Patent is hereby corrected as shown below:

| | |
|---|---|
| Col. 1, line 25 | Delete "for" and substitute --or-- |
| Col. 2, line 2 | Delete "Cn" and substitute --CN-- |
| Col. 3, line 20 | Delete "amine" and substitute --amide-- |
| Col. 5, line 25 | Before "compounds" delete "the" |
| Col. 9, line 68 | Delete "1,1'-dimethyl-spiro[1H-1,4-benzodiazepine-" |
| Col. 13, line 20 | Delete " $\leqq$ " and substitute -- $\leq$ -- |
| Col. 15, line 63 | Delete "is" and substitute --it-- |
| Col. 16, line 6 | Delete "(3)" and substitute --(3H)-- |
| Col. 17, line 1 | Delete "yeld" and substitute --yield-- |
| Col. 17, line 6 | Delete "chloro" and substitute --Chloro-- |
| Col. 17, line 40 | Delete "benzoly" and substitute --benzoyl-- |
| Col. 19, line 57 | Delete "20" and substitute --25-- |
| Col. 20, line 50 | Correct spelling of --aminoacetophenone-- |
| Col. 20, line 55 | Delete "ethylene" and substitute --methylene-- |
| Col. 21, line 54 | Delete "3,4" and substitute --3,4'-- |
| Col. 23, line 45 | After "chloro-" delete "1b" |
| Col. 32, line 21 | Delete "either" and substitute --ether-- |

UNITED STATES PATENT AND TRADEMARK OFFICE
CERTIFICATE OF CORRECTION

PATENT NO. : 4,647,560
DATED : March 3, 1987
INVENTOR(S) : Karl-Heinz Boltze, et al.

It is certified that error appears in the above-identified patent and that said Letters Patent is hereby corrected as shown below:

| | |
|---|---|
| Col. 32, line 32 | Before "form" insert --the-- |
| Col. 45, Examples 67 and 68 | Delete "benzyloxycarbonyl" and substitute --benzoyloxycarbonyl-- |
| Col. 51, Example 84 | After "cyclohexanoyl" delete ")" |
| Col. 57, lines 22, 24 and 29 | Delete "]" and substitute --[-- |
| Col. 58, line 10 | Delete end of formula and substitute |

Signed and Sealed this

Fifteenth Day of September, 1987

*Attest:*

DONALD J. QUIGG

*Attesting Officer*   *Commissioner of Patents and Trademarks*